United States Patent
Yerxa et al.

(10) Patent No.: US 7,531,525 B2
(45) Date of Patent: *May 12, 2009

(54) P¹-(2'-DEOXYCYTIDINE 5'-)P⁴-(URIDINE 5'-)TETRAPHOSPHATE, TETRA-(ALKALI METAL) SALT, FOR TREATING CYSTIC FIBROSIS

(75) Inventors: Benjamin R. Yerxa, Raleigh, NC (US); Ward M. Peterson, Morrisville, NC (US); Janet L. Rideout, Fuquay-Varina, NC (US); William Pendergast, Durham, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/690,385

(22) Filed: Mar. 23, 2007

(65) Prior Publication Data

US 2007/0197454 A1    Aug. 23, 2007

Related U.S. Application Data

(60) Division of application No. 10/962,016, filed on Oct. 7, 2004, now Pat. No. 7,223,744, which is a continuation-in-part of application No. 10/397,795, filed on Mar. 25, 2003, now Pat. No. 6,818,629, which is a continuation-in-part of application No. 09/774,752, filed on Jan. 30, 2001, now Pat. No. 6,596,725, which is a continuation-in-part of application No. 09/101,395, filed as application No. PCT/US98/02702 on Feb. 6, 1998, now Pat. No. 6,348,589.

(51) Int. Cl.
*A61K 31/7072* (2006.01)
*C07H 19/10* (2006.01)

(52) U.S. Cl. .............................. 514/51; 514/49; 514/50; 536/26.22

(58) Field of Classification Search .................... 514/51
See application file for complete search history.

(56) References Cited

U.S. PATENT DOCUMENTS

| 5,837,861 | A  | 11/1998 | Pendergast et al. |
| 6,040,297 | A  | 3/2000  | De Flora et al. |
| 6,258,374 | B1 | 7/2001  | Friess et al. |
| 6,277,855 | B1 | 8/2001  | Yerxa |
| 6,319,908 | B1 | 11/2001 | Yerxa et al. |
| 6,323,187 | B1 | 11/2001 | Yerxa et al. |
| 6,348,589 | B1 | 2/2002  | Pendergast et al. |
| 6,548,658 | B2 | 4/2003  | Yerxa et al. |
| 6,555,675 | B2 | 4/2003  | Rideout et al. |
| 6,596,725 | B2 | 7/2003  | Peterson et al. |
| 6,673,779 | B2 | 1/2004  | Jacobus et al. |
| 6,696,425 | B2 | 2/2004  | Yerxa et al. |
| 6,818,629 | B2 | 11/2004 | Peterson et al. |
| 6,867,199 | B2 | 3/2005  | Rideout et al. |
| 6,977,246 | B2 | 12/2005 | Pendergast et al. |
| 7,034,052 | B2 | 4/2006  | Man et al. |
| 7,078,391 | B2 | 7/2006  | Peterson et al. |
| 2005/0085439 | A1 | 4/2005 | Yerxa et al. |

FOREIGN PATENT DOCUMENTS

| WO | WO 96/02554 A1 | 2/1996 |
| WO | WO 96/40059 A1 | 12/1996 |
| WO | WO 98/15563 A1 | 4/1998 |
| WO | WO 98/34942 A2 | 8/1998 |
| WO | WO 98/55494 A1 | 12/1998 |
| WO | WO 00/30629 A2 | 6/2000 |
| WO | WO 01/87913 C2 | 11/2001 |
| WO | WO 02/060454 A2 | 8/2002 |

OTHER PUBLICATIONS

Blaug, et al., "P2Y2 receptor agonists induce prolonged calcium, membrane voltage, conductance and fluid absorption increases in bovine RPE," *IOVS*, 41(4):S136 (2000) XP001088187.

Burnstock, et al., "P2 purinergic receptors: Modulation of cell function and therapeutic potential," *Journal of Pharmacology and Experimental Therapeutics* 295(3) 862-869 (2002) XP002208652.

(Continued)

*Primary Examiner*—Shaojia Anna Jiang
*Assistant Examiner*—Jonathan S Lau
(74) *Attorney, Agent, or Firm*—Howrey LLP; Viola T. Kung

(57) ABSTRACT

The present invention provides a method of treating edematous retinal disorders. The method comprises administration of a pharmaceutical formulation comprising a hydrolysis-resistant P2Y receptor agonist to stimulate the removal of pathological extraneous fluid from the subretinal and retinal spaces and thereby reduce the accumulation of said fluid associated with retinal detachment and retinal edema. The P2Y receptor agonist can be administered with therapeutic and adjuvant agents commonly used to treat edematous retinal disorders. The present invention also provides a method of treating cystic fibrosis. The present invention further provides $P^1$-(2'-deoxycytidine 5'-)$P^4$-(uridine 5'-) tetraphosphate, tetra-(alkali metal) salts such as tetrasodium, tetralithium, tetrapotassium, and mixed (tetra-alkali metal) salts. The present further provides a pharmaceutical formulation comprising a $P^1$-(2'-deoxycytidine 5'-)$P^4$-(uridine 5'-) tetraphosphate, tetra-(alkali metal) salt, in a pharmaceutically acceptable carrier.

5 Claims, 9 Drawing Sheets

OTHER PUBLICATIONS

Ferris, et al., "Oligomerization reactions of deoxyribonucleotides on montmorillonite clay: the effect of mononucleotide structure on phosphodiester bond formation," *Origins Life Evol. Biosphere*, 19(6):609-619 (1989) XP001085277.

Maminishkis, et al., "Purinoceptor agonists increase fluid clearance out of subretinal space (SRS) blebs in vivo," *IOVS*, 41(4):S136 (2000) XP001083820.

Maminishkis et al., "The P2Y2 Receptor Agonist INS37217 Stimulates RPE Fluid Transport In Vitro and Retinal Reattachment in Rat," *IOVS*, 43(11), 3555-3566, 2002.

Peterson, et al., "Extracellular ATP activates calcium signaling, ion, and fluid transport in retinal pigment epithelium," *Journal of Neuroscience*, 17:(7)2324-2337 (1997) XP001087693.

Sillero, et al., (2',3'-Dideoxynucleoside triphosphates (ddNTP) and di-2',3'-dideoxynucleoside tetraphosphates (ddNp4ddN) behave differently to the corresponding . . . , *Biochimica et Biophysica Acta*, 1334(2-3):191-199 (1997) XP002208651.

Theoclitou, et al., "Characterization of stress protein LysU. Enzyme synthesis of diadenosine 5',5'''-P1 ,P4-tetraphosphate (Ap4A) analogs by LysU, *J. Chem. Soc., Perkins Trans.* 1(16):2009-2019 (1996) XP001087969.

Williams, M., "P2 Receptors as drug discovery targets," *Am. Chem. Soc.* 220th, Medi-185 (2000) XP001085299.

Yerxa, et al., *J. Pharm and Experimental Therapeutics*, 302, 871-80, (2002).

Zhavrid, et al., "Dicytidine-5'-pyrophosphates with antivirus activity," STN No. 123:314403, XP002208653 abstract, SU 689 202 A (Belorusskij Nauchno-Issledovatelskij Institut Epidemiologii I Mikrobio), (Oct. 30, 1993).

P¹-(2'-DEOXYCYTIDINE 5'-)P⁴-(URIDINE 5'-)TETRAPHOSPHATE, TETRA-(ALKALI METAL) SALT, FOR TREATING CYSTIC FIBROSIS

This application is a divisional of U.S. application Ser. No. 10/962,016, filed Oct. 7, 2004, now U.S. Pat. No. 7,223,744; which is a continuation-in-part of U.S. application Ser. No. 10/397,795, filed Mar. 25, 2003, now U.S. Pat. No. 6,818,629; which is a continuation-in-part of U.S. application Ser. No. 09/774,752, filed Jan. 30, 2001, now U.S. Pat. No. 6,596,725; which is a continuation-in-part of U.S. application Ser. No. 09/101,395, filed Jul. 10, 1998, now U.S. Pat. No. 6,348,589; which was the National Stage of International Application No. PCT/US98/02702, filed Feb. 6, 1998, published Aug. 13, 1998 under PCT Article 21(2) in English. All U.S. applications and patents cited herein are specifically incorporated herein by reference in their entirety.

TECHNICAL FIELD

This invention relates to a method of treating edematous retinal disorders. Specifically, this invention relates to a method of removing pathological fluid accumulation in subretinal and intra-retinal spaces. This invention also relates to dinucleoside polyphosphate salts, such as a $P^1$-(2'-deoxycytidine 5'-)$P^4$-(uridine 5'-) tetraphosphate tetra-(mixed alkali metal) salt. This invention further relates to a pharmaceutical formulation comprising one or more dinucleoside polyphosphate salts such as $P^1$-(2'-deoxycytidine 5'-)$P^4$-(uridine 5'-) tetraphosphate tetra-(alkali metal) salt, in a pharmaceutically-acceptable carrier.

BACKGROUND OF THE INVENTION

The retinal pigment epithelium (RPE) lies in the back of the vertebrate eye and forms a barrier that separates the retina from the choroidal blood supply. A critical function of the RPE is to maintain and regulate the hydration of the subretinal space, the extracellular volume that exists between the retina and the RPE. (Marmor, pp. 3-12, in *The Retinal, Pigment Epithelium*, Eds. M. F. Marmor and T. J. Wolfensberger, Oxford University Press, New York, (1998)). This function is achieved by the regulated transport of fluid, ions, and metabolites between the subretinal space and the choroidal blood supply. (Marmor, pp. 420-438, in *The Retinal Pigment Epithelium*, Eds. M. F. Marmor and T. J. Wolfensberger, Oxford University Press, New York, (1998); Pederson, pp. 1955-1968, in *Retina*, Ed. S. J. Ryan, Mosby, St. Louis, (1994)). Like all epithelia, the RPE contains two functionally and anatomically distinct membranes: an apical membrane that faces the retina, and a basolateral membrane that faces the choroidal blood supply. In the normal retina, fluid is absorbed across the RPE in the direction of the subretinal space to the choroid. This active absorption of fluid by the RPE, often referred to as the "RPE pump," plays a critical role in maintaining proper attachment of photoreceptors to the apical membrane of the RPE by pumping fluid out of the retinal spaces. (Marmor, pp. 1931-1954, in *Retina*, Ed. S. J. Ryan, Mosby, St. Louis, (1994); Hughes, et al., pp. xvii, 745, in *The Retinal Pigment Epithelium*, Eds. M. F. Marmor and T. J. Wolfensberger, Oxford University Press, New York, (1998)).

Retinal detachment is characterized by abnormal accumulation of fluid in the subretinal space leading to detachment of the retina from the underlying retinal pigment epithelium. Retinal edema refers to abnormal accumulation of fluid within the retina itself. Retinal detachment or edema in the central part of the retina (macula) produces significant loss of vision, and can ultimately lead to irreversible blindness. (Yanoff and Duker, *Ophthalmology*, Mosby, Philadelphia, (1999); Wilkinson, et al., *Michels'Retinal Detachment*, 2$^{nd}$ ed. Mosby, St. Louis, (1997)) A wide variety of ocular pathologies can result in retinal detachment or retinal edema. The most common type of retinal detachment is rhegmatogenous retinal detachment, which occurs as a result of single or multiple tears or holes in the retina that permit liquefied vitreous to enter into the subretinal space and create a retinal detachment.

There are no pharmacological approaches employed in the treatment of rhegmatogenous retinal detachment (RRD). The only current treatments for RRD are surgical (scleral buckling, pneumatic retinopexy, or vitrectomy). (Wilkinson, *Michels'Retinal Detachment*, 2nd ed., Mosby, St. Louis, (1997)). There are two vital components for successful RRD surgery: reattachment of the retina and repair of the retinal break. The principal difference among the three surgical techniques for treating RRD is in the method employed to facilitate retinal reattachment.

Scleral buckle uses an extraocular buckle (usually a silicone sponge or solid silicone) that is sewn to the sclera towards the detached retina (Wilkinson, et al., *Michels'Retinal Detachment*, 2nd ed., Mosby, St. Louis (1997)). The retina usually reattaches over a period of a few days, but may take up to a few weeks. The surgeon may elect to drain the subretinal fluid at the time of operation by inserting a needle through the sclera, choroid, and RPE. In general, the buckle remains permanently sewn to the sclera. In pneumatic retinopexy, a gas bubble is injected directly into the vitreous, and the head is positioned so that the gas bubble acts as a tamponade and covers the retinal break. (Tomambe and Hilton, *Ophthalmology* 96(6):772-83 (1989)). The subretinal fluid usually resolves within 1-2 days, but precise head positioning is required to insure that the bubble covers the retinal break. (Tomambe, 10 et al., *Am. J. Opthalmol.* 127(6):741-3 (1999)). Vitrectomy is usually used for complex RRD associated with vitreous traction or hemorrhage, but is occasionally used for simple RRD (Chang, pp. 8.34.1-8.34.6, in *Ophthalmology*, Eds. M. Yanoff and J. S. Duker, Mosby, Philadelphia, (1999)). The procedure involves making three small incisions through the sclera to allow the introduction of instruments in the vitreous cavity. The vitreous is removed and replaced with a special saline solution. Depending on the type and cause of the detachment, a variety of instruments and techniques are then used to reattach the retina. For simple detachments, the retina is flattened via anterior drainage of the subretinal space by insertion of a needle through the retinal tear.

Scleral buckle and vitrectomy often require general anesthesia and can involve hospitalization. Pneumatic retinopexy is usually done in the physician's office, but requires patient compliance for success. (Hilton and Tomambe, *Retina* 11(3): 285-94 (1991); Hilton and Brinton, pp. 2093-2112, in *Retina*, Ed. Stephen J. Ryan, Mosby, Philadelphia, (1999); Han, et al., *Am. J. Opthalmol.* 126(5):658-68 (1998)). Depending on the surgical technique and the surgeon, success rates can vary following a single surgery, with lower rates for pneumatic retinopexy and higher rates for scleral buckle. (Tomambe, et al., *Am. J. Opthalmol.* 127(6):741-3 (1999); Han, et al., *Am. J. Opthalmol.* 126(5):658-68 (1998)). The success of retinal detachment surgery is measured in terms of retinal reattachment at any point following surgery (ranging from hours to weeks). Parameters such as visual outcome and patient quality-of-life are not used to assess success of retinal detachment surgery.

The conditions that are commonly associated with the more severe forms of intra-retinal edema are diabetic macular edema, exudative age-related macular degeneration (AMD) and clinically significant cystoid macular edema. (Jampol and Po, pp. 999-1008, in *Retina*, Ed. S. J. Ryan, Mosby, St. Louis, (1994)). Other pathological conditions associated with abnormal fluid accumulation in intra-retinal or subretinal spaces include uveitis, central and branch vein occlusion, retinitis pigmentosa, central serous retinopathy, CMV retinitis, and choroidal melanoma. Physical trauma associated with ocular injury following certain surgical procedures (such as cataract surgery) can also produce retinal detachment or edema. (Ahmed and Ai, pp. 8.34.1-8.34.6, in *Ophthalmology*, Eds. M. Yanoff and J. Duker, Mosby, Philadelphia, (1999)).

Intra-retina accumulation of fluid in the macula results in decreased visual acuity and is the most common cause of vision loss in patients with diabetic retinopathy, AMD and other ischemic retinopathies such as branch and central retinal vein occlusion. (Jampol and Po, pp. 999-1008, in *Retina*, Ed. Stephen J. Ryan, Mosby, St. Louis, (1994); Kent, et al., *Br. J. Opthalmol.* 84(5):542-5 (2000)). Macular edema is a frequent complication of uveitis and is commonly seen in patients with retinitis pigmentosa. (Rothova, et al., *Br. J. Opthalmol.* 80(4):332-6 (1996); Fetkenhour, et al., *Trans. Am. Acad. Opthalmol. Otolaryngol.* 83 (3) Pt 1: OP515-21 (1977)). Macular edema is also a major cause of decreased vision following intraocular surgery (called cystoid macular edema). (Miyake, *Surv. Opthalmol* 28 Suppl:554-68 (1984)). Accumulation of intra-retina fluid is believed to result from a breakdown of the inner and/or outer blood-retinal barrier. (Kent, et al., *Br. J. Opthalmol.* 84(5): 542-5 (2000)). The inner retinal barrier consists of endothelial cells of the retinal vasculature and the outer barrier comprises the retinal pigment epithelium. Breakdown of the blood-retinal barrier can result in focal leakage of fluid from the vasculature and fluid accumulation within retinal layers or in the subretinal space. The present treatments for retinal edema include systemic and topical administrations of corticosteroid, acetazolamide, and non-steroidal anti-inflammatory drugs, as well as surgical options such as vitrectomy, grid, and focal laser photocoagulation. These therapies show limited utility in patients.

Although modern day RRD surgery has a relatively high success rate (60-90%), it is thought that a pharmaceutical composition that can reattach the retina in cases where surgery failed would be of enormous patient benefit. In addition, if the pharmaceutical composition can reattach the retina in the absence of surgical intervention, it would be most therapeutically useful, particularly in the treatment of rhegmatogenous retinal detachment.

A number of pharmacological and surgical approaches are employed to treat cystoid and diabetic macular edema, but they are generally considered empirical and often ineffective. Non-specific anti-inflammatory treatment is used for all types of macular edema, except in cases associated with ischemic retinopathies in which laser treatment is indicated (Kent, et al., *Br. J. Opthalmol.* 84 (5):542-5 (2000)). Corticosteroids are frequently used to treat macular edema, but were shown to be ineffective in a randomized, placebo controlled study (Flach, et al., *Am. J. Opthalmol.* 103(4):479-86 (1987); Flach, et al., *Ophthalmology* 97(10):1253-8 (1990)). Acetazolamide also alleviates certain types of macular edema and is postulated to work via activation of the RPE pump, but systemic tolerance to acetazolamide is poor. (Cox, et al., *Arch. OphthaZmoZ.* 106 (g):1190-5 (1988)). Focal or grid laser photocoagulation is commonly used to reduce retinal vascular leakage associated with diabetic retinopathy, and is useful in limited cases. (Ip, et al., *In Ophthalmology*, London; Philadelphia: Mosby, 8.4.1-8.4.2 (1999); The Diabetic Retinopathy Study Research Group, *Ophthalmology* 88 (7):583-600 (1981); Early Treatment Diabetic Retinopathy Study Research Group, *Arch. Opthalmol.* 103(12):1796-806 (1985); The Branch Vein Occlusion Study Group, *Am. J. Opthalmol.* 98(3):271-82 (1984)). In addition, vitrectomy is employed to treat diabetic retinopathies associated with vitreal hemorrhages and/or vitreoretinal traction. (Wilkinson, et al, *Michels'Retinal Detachment,* 2nd ed., Mosby, St. Louis, (1997)). There remains a large unmet medical need for a safe, effective treatment of macular edema. (Kent, et al., *Br. J. Opthalmol.* 84(5):542-5 (2000)).

Peterson, et al. (*J. Neurosci.* 17:2324-37 (1997)) suggest that UTP (or perhaps ATP) could be used therapeutically to reduce the pathological accumulation of fluid in the subretinal space. However, both ATP and UTP are rapidly degradable by ubiquitous extracellular nucleotidases. Therefore, in order for ATP and UTP to be efficacious in the treatment of retinal detachment, these compounds need to be delivered directly into the subretinal space. Drug delivery into the subretinal space is widely regarded to be unacceptably risky for patients because it involves the insertion of a needle between the retina and RPE, which can result in complications and blindness. In order for ATP or UTP to be therapeutically useful, it must be delivered into the intravitreal cavity, which is a much less invasive procedure. However, in order for ATP or UTP to reach the RPE apical membrane, it must diffuse across the retina. It is unknown if intravitreal ATP or UTP is degraded by the time it reaches the RPE apical membrane and therefore effective in stimulating retinal reattachment. The present examples show that intravitreal UTP is ineffective in stimulating retinal reattachment and that the present method is effective in stimulating retinal reattachment.

SUMMARY OF THE INVENTION

The present invention is directed to pharmaceutical compositions and methods of use thereof for stimulating removal of extraneous fluid in the retina or subretinal space in a subject in need of such treatment are disclosed. The methods and compositions disclosed in the present invention are used to stimulate removal of extraneous intra-retinal or subretinal fluid for any reason, including, but not limited to, primary and adjunctive treatments of rhegmatogenous retinal detachment, serous retinal detachment, all forms of cystoid macular edema (uveitis, post-surgical, central and branch vein occlusion, and inherited retinal diseases such as retinitis pigmentosa), and all forms of retinal and macular edema (proliferative and non-proliferative, exudative age-related macular degeneration, and retinopathy of prematurity).

The present invention discloses methods of treating a subject with edematous retinal disorders such as retinal detachment or retinal edema by administering a pharmaceutical composition comprising a hydrolysis-resistant P2Y receptor agonist via systemic or topical administration such as intravitreal injection, intravitreal sustained release or delivery, ocular surface instillation, transcleral injection or infusion, or systemic injection or infusion.

The pharmaceutical formulations useful in this invention comprise adenine-, uridine-, and cytidine-containing dinucleoside polyphosphate salts, and derivatives thereof, and hydrolysis-resistant mononucleoside triphosphate salts, which are selective agonists of the P2Y receptor on epithelial cells of the retinal pigment epithelium.

The present invention is also directed to poly-(alkali metal) salts, poly-ammonium salts, and poly-(quaternary ammonium) salts of dinucleoside polyphosphates. The dinucleoside polyphosphate salts of the present invention include $P^1$-(2'-deoxycytidine 5'-)$P^4$-(uridine 5'-) tetraphosphate (i.e., $dCP_4U$) tetra-(alkali metal) salts, such as -tetrasodium, -tetralithium, -tetrapotassium, and mixed tetra-(alkali metal) salts of dCP4U; $P^1$-(2'-deoxycytidine 5'-)$P^3$-(uridine 5'-) triphosphate (i.e., $dCP_3U$) tri-(alkali metal) salt, or tri-ammonium salt, or tri-(quaternary ammonium) salt; and $P^1$-(2'-deoxycytidine 5'-)$P^2$-(uridine 5'-) diphosphate (i.e., $dCP_2U$) di-(alkali metal) salt, di-ammonium salt, or di-(quaternary ammonium) salt. The poly-(alkali metal) salts of dinucleoside polyphosphates (e.g., tetra-(alkali metal) salts of $dCP_4U$, tri-(alkali metal) salts of $dCP_3U$, and di-(alkali metal) salts of $dCP_2U$) are water-soluble, nontoxic, and easy to handle during manufacture. These dinucleoside polyphosphate alkali metal salts in which each phosphate of the polyphosphate chain is in its anionic form are more resistant to hydrolysis than the various-acid salt ($H^+$) forms, therefore, the poly-(alkali metal) salts provide an improved stability and a longer shelf life for storage. The poly-ammonium salts, including quaternary ammonium salts, of dinucleoside polyphosphates are also useful materials of this invention.

Another aspect of the present invention is a pharmaceutical formulation comprising one or more dinucleoside polyphosphate salts (such as $P^1$-(2'-deoxycytidine 5-)$P^4$-(uridine 5'-) tetraphosphate tetra-(alkali metal) salt, or -tetra-ammonium salt, or -tetra-(quaternary ammonium) salt) in a pharmaceutically acceptable carrier, in the form of an aqueous, a gel, a gel-like, a two-phase suspension, or a solid formulation.

Similarly, the present invention includes a pharmaceutical formulation comprising a dinucleoside triphosphate salt such as $P^1$-(2'-deoxycytidine 5'-)$P^3$-(uridine 5'-)triphosphate tri-(alkali metal) salt, or tri-ammonium salt, or tri-(quaternary ammonium) salt in a pharmaceutically acceptable carrier, in the form of an aqueous, a gel, a gel-like, a two-phase suspension, or a solid formulation. The present invention further includes a pharmaceutical formulation comprising a dinucleoside diphosphate salt such as $P^1$-(2'-deoxycytidine 5'-)$P^2$-(uridine 5'-)diphosphate di-(alkali metal) salt, or di-ammonium salt, or di-(quaternary ammonium) salt) in a pharmaceutically acceptable carrier, in the form of an aqueous, a gel, a gel-like, a two-phase suspension, or a solid formulation.

DETAILED DESCRIPTION OF THE INVENTION

Figure 1:
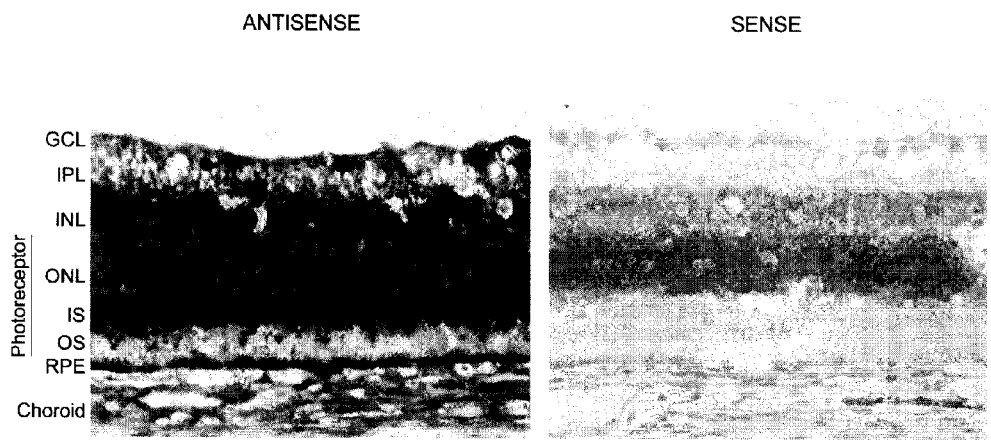
FIG. 1 represents cellular localization of $P2Y_2$ receptor mRNA in fresh frozen cross sections of albino rabbit retina/RPE/choroid tissue using nonisotopic in situ hybridization techniques. Specifically, a representative in situ hybridization result from antisense and sense digoxigenin (DIG)-labeled riboprobes engineered based on the $P2Y_2$ receptor mRNA sequence is shown. GCL: ganglion cell layer. IPL: inner plexiform layer. INL: inner nuclear layer. ONL: outer nuclear layer. IS: inner segments. OS: outer segments.

The present invention provides a method of increasing fluid absorption across the retinal pigment epithelium (RPE) to facilitate the removal of extraneous intraretinal or subretinal fluid from the posterior portion of the eye to treat diseases that lead to retinal detachment and retinal edema. The apical (retinal-facing) membrane of the RPE contains P2Y receptors that can be activated to stimulate fluid transport across the RPE in the direction from the subretinal space to the choroidal blood supply, so as to facilitate the removal of subretinal fluid in retinal detachment. The present method comprises administering to a subject a P2Y receptor agonist that is hydrolysis-resistant in an amount effective to stimulate the removal of pathological fluid accumulation in intra-retinal and subretinal spaces associated with edematous retinal disorders. Activation of P2Y receptors by such agonists is associated with elevated intracellular calcium levels and increased fluid transport across the RPE.

The P2Y receptor agonist is administered with or without other therapeutic and adjuvant agents commonly used to treat or manage retinal detachment and retinal edema. An effective dose is the amount of such agonist necessary to activate P2Y receptors at the retinal-facing (apical) membrane of retinal pigment epithelial cells and to enhance fluid absorption (retinal-to-choroidal direction) across the RPE.

The method of the present invention is useful for the prevention, management and/or treatment of all disorders associated with retinal detachment and retinal edema, including but not limited to rhegmatogenous retinal detachment, serous retinal detachment, all forms of cystoid macular edema (uveitis, post-surgical, central and branch vein occlusion, and inherited retinal diseases such as retinitis pigmentosa), and all forms of retinal and macular edema (proliferative and non-proliferative diabetic macular edema, exudative age-related macular degeneration, and retinopathy of prematurity).

This invention provides a method of administering to a subject a pharmaceutical composition comprising a P2Y receptor agonist for removing pathological fluid accumulation in subretinal and intra-retinal spaces. P2Y receptor agonists useful for the present method are hydrolysis-resistant compounds such that they are not degraded by the time they reach the RPE apical membrane and therefore they are effective in stimulating retinal reattachment. P2Y receptor agonists useful for the present method include dinucleoside polyphosphate salts, hydrolysis-resistant mononucleoside triphosphate salts and their analogues, which activate P2Y$_1$, P2Y$_2$, P2Y$_4$, P2Y$_6$, and/or P2Y$_{11}$, and preferably P2Y$_2$ receptors.

Description of Compounds

Dinucleoside polyphosphate salts useful for this invention are non-toxic compounds of general Formula I or pharmaceutically acceptable non-toxic derivatives thereof:

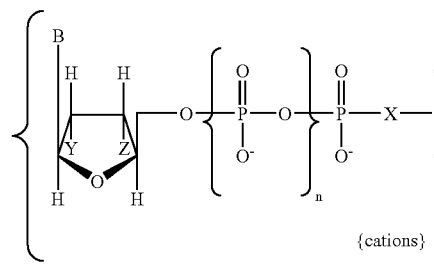

Formula I where sum of cationic charges=m+n+2 wherein:

X is oxygen, methylene, halomethylene, dihalomethylene (with halo being fluoro or chloro preferred), or imido;

n=0, 1 or 2;

m=0, 1 or 2;

n+m=0, 1, 2, 3, or 4;

Z=OH, N$_3$ or H;

Z'=OH, N$_3$ or H;

Y=OH, N$_3$ or H;

Y'=OH, N$_3$ or H;

cations are independently selected from the group consisting of sodium, potassium, lithium, calcium, magnesium, ammonium, and quaternary ammonium; preferred cations are sodium, potassium, and lithium; more preferred cations are sodium and potassium;

with the proviso that no more than one azide (N$_3$) group is present on any one furanose moiety of a compound of Formula I;

B and B' are each independently a purine residue or a pyrimidine residue, as defined in Formula Ia or Ib, linked through the 9- or 1-position, respectively;

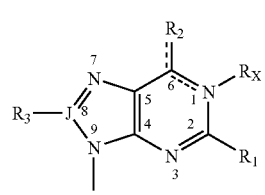

Formula Ia wherein:

R$_1$ is selected from the group consisting of: hydrogen, fluoro, chloro, bromo, cyano, azido, amino, N-alkylamino, N,N-dialkylamino, N-cycloalkylamino, N-aralkylamino, N-arylamino, N-acylamino (amide), N-alkyl-N-acylamino (N-alkyl amide), N-cycloalkyl-N-acylamino (N-cycloalkyl amide), N-aralkyl-N-acylamino (N-aralkyl amide), N-aryl-N-acylamino (N-aryl amide), alkyloxy, aralkyloxy, aryloxy, alkylthio, arylthio, and aralkylthio, wherein such a substitutent on the nitrogen, oxygen, or sulfur contains up to a maximum of 20 carbon atoms, with or without unsaturation; optionally, up to two heteroatoms selected from the group consisting of oxygen, NH, and sulfur are substituted in place of carbon units in such a substitution; optionally, said N,N-dialkylamino groups are linked to form a heterocycle of 3 to 7 members;

R$_2$ is hydroxy, alkenyl, oxo, amino, mercapto, thione, alkylthio, arylthio, aralkylthio, acylthio, alkyloxy, aryloxy, aralkyloxy, acyloxy, N-alkylamino, N,N-dialkylamino, N-cycloalkylamino, N-aralkylamino, N-arylamino, N-acylamino (amide), N-alkyl-N-acylamino (N-alkyl amide), N-cycloalkyl-N-acylamino (N-cycloalkyl amide), N-aralkyl-N-acylamino (N-aralkyl amide), N-aryl-N-acylamino (N-aryl amide), or a heterocyclic moiety containing 3 to 10 carbons atoms;

R$_x$ is O, H or is absent;

R$_2$ and R$_x$ are optionally taken together to form a 5-membered fused imidazole ring of a 1,N$^6$-etheno adenine derivative, optionally substituted on one or both of the 4- or 5-positions of the etheno moiety with alkyl, aryl or aralkyl moieties as defined below;

R$_3$ is selected from the group consisting of hydrogen, fluoro, chloro, bromo, cyano, azido, amino, N-alkylamino, N,N-dialkylamino, N-cycloalkylamino, N-aralkylamino, N-arylamino, N-acylamino (amide), N-alkyl-N-acylamino (N-alkyl amide), N-cycloalkyl-N-acylamino (N-cycloalkyl amide), N-aralkyl-N-acylamino (N-aralkyl amide), N-aryl-N-acylamino (N-aryl amide), alkyloxy, aralkyloxy, aryloxy, alkylthio, arylthio, and aralkylthio, wherein such a substitutent on the nitrogen, oxygen, or sulfur contains up to a maximum of 20 carbon atoms, with or without unsaturation; optionally, up to two heteroatoms selected from the group consisting of oxygen, NH, and sulfur are substituted in place of carbon units in such a substitution; optionally, said N,N-dialkylamino groups are linked to form a heterocycle of 3 to 7 members; or absent;

J is carbon or nitrogen, with the provision that when J is nitrogen, R$_3$ is not present;

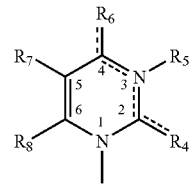

Formula Ib wherein:

R$_4$ is hydroxy, oxo, mercapto, thione, amino, cyano, arylalkoxy, alkylthio, alkoxy, N-alkylamino, N,N-dialkylamino, N-cycloalkylamino, N-aralkylamino, N-arylamino, N-acylamino (amide), N-alkyl-N-acylamino (N-alkyl amide), N-cycloalkyl-N-acylamino (N-cycloalkyl amide), N-aralkyl-N-acylamino (N-aralkyl amide), N-aryl-N-acylamino (N-aryl amide), or a heterocyclic moiety containing 3 to 10 carbons atoms; optionally, said N,N-dialkylamino groups are linked to form a heterocycle of 3 to 7 members;

$R_5$ is hydrogen, acetyl, benzoyl, alkyl, alkanoyl, aroyl, or absent;

$R_6$ is hydroxy, oxo, mercapto, thione, amino, cyano, arylalkoxy, alkylthio, alkoxy, aryloxy, N-alkylamino, N,N-dialkylamino, N-cycloalkylamino, N-aralkylamino, N-arylamino, N-acylamino (amide), N-alkyl-N-acylamino (N-alkyl amide), N-cycloalkyl-N-acylamino (N-cycloalkyl amide), N-aralkyl-N-acylamino (N-aralkyl amide), N-aryl-N-acylamino (N-aryl amide), or a heterocyclic moiety containing 3 to 10 carbons atoms; optionally said N,N-dialkylamino groups are linked to form a heterocycle; wherein said N-, O- or S-alkyl group is optionally linked to $N^3$ to form a saturated or unsaturated heterocyclic ring of 5 to 7 members, with or without substitutents; or $R_5$ and $R_6$ are taken together to form a 5-membered fused imidazole ring between positions 3 and 4 of the pyrimidine ring and form a 3,$N^4$-ethenocytosine derivative, wherein said etheno moiety is optionally substituted on one or both of the 4- or 5-positions with a moiety selected from the group consisting of: alkyl, aryl, aralkyl, aryloxy, alkyloxy, and aralkoxy;

$R_7$ is selected from the group consisting of: hydrogen, hydroxy, cyano, nitro, alkyl, aralkyl, alkenyl, aralkenyl, alkynyl, aryl, aralkynyl, halogen, $CF_3$, allylamino, bromovinyl, ethyl propenoate, propenoic acid and alkyl or aryl esters thereof; or $R_6$ and $R_7$ optionally form a 5 or 6-membered saturated or unsaturated ring bonded through N or O or S at $R_6$, such ring optionally contains alkyl, aralkyl or aryl substitutents;

$R_8$ is selected from the group consisting of hydrogen, fluoro, chloro, bromo, cyano, azido, amino, carboxy, carbalkoxy, carbobenzyloxy, carboxamido, N-alkylcarboxamido, N-alkylamino, N,N-dialkylamino, N-cycloalkylamino, N-aralkylamino, N-arylamino, N-acylamino (amide), N-alkyl-N-acylamino (N-alkyl amide), N-cycloalkyl-N-acylamino (N-cycloalkyl amide), N-aralkyl-N-acylamino (N-aralkyl amide), N-aryl-N-acylamino (N-aryl amide), alkyloxy, aralkyloxy, aryloxy, alkylthio, arylthio, or aralkylthio, wherein such a substitutent on the nitrogen, oxygen, or sulfur contains up to a maximum of 20 carbon atoms, with or without unsaturation; optionally, up to two heteroatoms selected from the group consisting of oxygen, NH, and sulfur are substituted in place of carbon units in such a substitution; optionally, said N,N-dialkylamino groups are linked to form a heterocycle of 3 to 7 members;

wherein the alkyls, alkenyls, and alkynyls are straight-chain, branched or cyclic; substituted or unsubstituted; and wherein the terms "ammonium salt" or "ammonium salts" are used to describe salts derived from ammonia as well as those derived from alkyl amines, dialkyl amines, trialkyl amines, aralkyl amines, aryl amines, dialkyl-aralkyl amines, etc., and the terms "quaternary ammonium salt" or "quaternary ammonium salts" are used to describe, but are not limited to: tetraalkylammonium salts, trialkylmonobenzylammonium salts, trialkylphenylammonium salts, dialkyldiarylammonium salts, tribenzylalkylammonium salts, trialkylaralkylammonium salts etc. and also salts where the ammonium cationic unit or quaternary ammonium cationic unit is part of, or bound to a polymer chain.

Examples of the substituted adenine derivatives of Formula Ia include adenine 1-oxide; 1,$N^6$-(4- or 5-substituted etheno) adenine; $N^6$-substituted adenine; or N-substituted 8-aminoadenine, where R' of the 6- or 8-HNR' groups are chosen from among: arylalkyl groups with the aryl moiety optionally functionalized as described below, alkyl, and alkyl groups with optional functional groups therein, such as: ([6-aminohexyl]carbamoylmethyl)-, and ω-acylated-amino (hydroxy, thiol or carboxy)alkyl derivatives where the acyl group is chosen from among, but not limited to, acetyl, trifluoroacetyl, benzoyl, substituted-benzoyl, etc., or the carboxylic moiety is present as its ester or amide derivative, for example, the ethyl or methyl ester or its methyl, ethyl or benzamido derivative. The ω-amino(hydroxy, thiol) moiety can be alkylated with a $C_{1-4}$ alkyl group.

For ease of reference, Formula I is drawn with the stereochemical properties shown, in which the furanosyl moieties are in the generally preferred ribose isomeric form and in the generally preferred D-furanose configuration, but the furanose moieties of a compound of Formula I can also be other furanose isomers and derivatives, and can be in the L-, or D- and L-configurations. Preferably, the nucleoside residues include the sugar moieties selected from the group consisting of: ribofuranosyl, arabinofuranosyl, 2'-deoxyribofuranosyl, 3'-deoxyribofuranosyl, 2',3'-dideoxyribofuranosyl, xylofuranosyl, 2'-deoxyxylofuranosyl and lyxofuranosyl; and these sugar moieties can be in the alpha- or beta-, and D- or L-configurations, and in general, are most preferably in the beta-D-configuration.

In the general structures of Formulae I, Ia and Ib above, the dotted lines in the 2- to 6-positions are intended to indicate the presence of single or double bonds in these positions; the relative positions of the double or single bonds being determined by whether the $R_x$, $R_2$ $R_4$, $R_5$ and/or $R_6$ substitutents are capable of keto-enol tautomerism.

In the general structures of Formula I above, the acyl groups comprise alkanoyl or aroyl groups. Preferably, the alkyl groups contain 1 to 8 carbon atoms, particularly 1 to 4 carbon atoms optionally substituted by one or more appropriate substitutents, as described below. The aryl groups including the aryl moieties of such groups as aryloxy are preferably phenyl groups optionally substituted by one or more appropriate substitutents, as described below. The above-mentioned alkenyl and alkynyl groups preferably contain 2 to 8 carbon atoms, particularly 2 to 6 carbon atoms, e.g., ethenyl or ethynyl, optionally substituted by one or more appropriate substitutents as described below.

Appropriate substitutents on the above-mentioned alkyl, alkenyl, alkynyl, aralkyl, and aryl groups are selected from halogen, hydroxy, $C_{1-4}$ alkoxy, $C_{1-4}$ alkyl, $C_{6-12}$ aryl, $C_{6-12}$ arylalkoxy, carboxy, cyano, nitro, sulfonamido, sulfonate, phosphate, sulfonic acid, amino and substituted amino wherein the amino is singly or doubly substituted by a $C_{1-4}$ alkyl, and when doubly substituted, the alkyl groups optionally being linked to form a heterocycle.

Dinucleoside polyphosphate salts of general Formula I include dinucleoside tetraphosphate-tetrasodium salts, -tetraammonium salts, -tetra(quaternary ammonium) salts, -tetrapotassium salts, -tetralithium salts, -trisodium/monopotassium salts, -disodium/dipotassium salts, -monosodium/tripotassium salts, -trisodium/monolithium salts, -disodium/dilithium salts, -monosodium/trilithium salts, disodium/monopotassium/monolithium salts, -dipotassium/monosodium/monolithium salts, and -dilithium/monosodium/monopotassium salts, wherein the anionic dinucleoside tetraphosphate components include, but are not limited to: $P^1,P^4$-di(uridine 5'-)tetraphosphate ($UP_4U$); $P^1$-

(cytidine 5'-) P$^4$-(uridine 5'-)tetraphosphate (CP$_4$U); P$^1$,P$^4$-di(adenosine 5'-) tetraphosphate; P$^1$-(adenosine 5'-)P$^4$-(uridine 5'-)tetraphosphate; P$^1$-(adenosine 5'-)P$^4$-(cytosine 5'-) tetraphosphate; P$^1$,P$^4$-di(ethenoadenosine)tetraphosphate; P$^1$-(uridine 5'-)P$^4$-(thymidine 5'-)tetraphosphate; P$^1$-(adenosine 5'-)P$^4$-(inosine 5'-)tetraphosphate; P$^1$,P$^4$-di(uridine 5'-)P$^2$,P$^3$-methylenetetraphosphate; P$^1$,P$^4$-di(uridine 5'-)P$^2$,P$^3$-difluoromethyl-enetetraphosphate; P$^1$,P$^4$-di(uridine 5'-)P$^2$,P$^3$-imidotetraphosphate; P$^1$,P$^4$-di(4-thiouridine5'-) tetraphosphate; P$^1$,P$^4$-di(3,N$^4$-ethenocytidine 5'-)tetraphosphate; P$^1$, P$^4$-di (imidazo[1,2-c]pyrimidine-5(6H)-one-2-(3-nitro)-phenyl-6-β-D-ribofuranoside 5'-)tetraphosphate; P$^1$-(inosine 5'-)P$^4$-(uridine 5'-)tetraphosphate; P$^1$-(4-thiouridine 5'-)P$^4$-(uridine 5'-)tetraphosphate; P$^1$-(cytosine β-D-arabinofuranoside 5'-) P$^4$-(uridine 5'-) tetraphosphate; P$^1$-(uridine 5'-)P$^4$-(xanthosine 5'-)tetraphosphate; P$^1$-(2'-deoxyuridine 5'-) P$^4$-(uridine 5'-)tetraphosphate; P$^{61}$-(3'-azido-3'-deoxythymidine 5'-) P$^4$-(uridine 5'-) tetraphosphate; P$^1$,P$^4$-di(3'-azido-3'-deoxythymidine 5'-)tetraphosphate; 2'(3')-benzoyl-P$^1$,P$^4$-di (uridine 5'-)tetraphosphate; P$^1$,P$^4$-di(2'(3')-benzoyl uridine 5'-)tetraphosphate; P$^1$-(2'-deoxyguanosine 5'-)P$^4$-(uridine 5'-)tetraphosphate; P$^1$-(2'-deoxyadenosine 5'-)P$^4$-(uridine 5'-)tetraphosphate; P$^1$-(2'-deoxyinosine 5'-)P$^4$-(uridine 5'-) tetraphosphate; P$^1$-(2'-deoxycytidine 5'-)P$^4$-(uridine 5'-) tetraphosphate (dCP$_4$U); P$^1$-(4-thiouridine 5'-)P$^4$-(2'-deoxyuridine 5'-)tetraphosphate; P$^1$-(8-azaadenosine-5'-)P$^4$-(uridine 5'-)tetraphosphate; P$^1$-(6-mercaptopurineriboside 5'-)P$^4$-(uridine 5'-)tetraphosphate; P$^1$-(6-mercaptopurineriboside 5'-)P$^4$-(2'-deoxyuridine 5'-) tetraphosphate; P$^1$-(4-thiouridine 5'-)P$^4$-(arabinocytidine 5'-) tetraphosphate; P$^1$-(adenosine 5'-)P$^4$-(4-thiomethyluridine 5'-)tetraphosphate; P$^1$-(2'-deoxyadenosine 5'-)P$^4$-(6-thiohexylpurineriboside 5'-)tetraphosphate, and P$^1$-(6-octyloxypurineriboside 5'-)P$^4$-(uridine 5'-)tetraphosphate. UP$_4$U tetrasodium salt, UP$_4$U trisodium/monopotassium salt, dCP$_4$U tetrasodium salt, and dCP$_4$U trisodium/monopotassium salt, are preferred dinucleoside tetraphosphate salts. These salts include hydrated and/or unhydrated salt forms. Preferably, the purity of an anionic dinucleoside tetraphosphate component with associated cations is >80% by weight, more preferably >90% by weight, and even more preferably >95% by weight in any hydrated- or non-hydrated solid form.

Dinucleoside polyphosphates of general Formula I also include dinucleoside triphosphate-trisodium salts, -triammonium salts, -tri(quaternary ammonium) salts, -tripotassium salts, -trilithium salts, -disodium/monopotassium salts, -monosodium/dipotassium salts, -disodium/monolithium salts, -monosodium/dilithium salts, and -monosodium/monopotassium/monolithium salts, wherein the anionic dinucleoside triphosphate components include, but are not limited to: P$^1$,P$^3$-di(uridine 5'-)triphosphate (UP$_3$U); P$^1$-(cytidine 5'-)P$^3$-(uridine 5'-)triphosphate; P$^1$,P$^3$-di(adenosine 5'-)triphosphate; P$^1$-(adenosine 5'-)P$^3$-(uridine 5'-)triphosphate; P$^1$-(adenosine 5'-)P$^3$-(cytidine 5'-)triphosphate; P$^1$,P$^3$-di(ethenoadenosine)triphosphate; P$^1$-(uridine 5'-)P$^3$-(thymidine-5'-)triphosphate; P$^1$-(adenosine 5'-)P$^3$-(inosine 5'-)triphosphate; P$^1$,P$^3$-di(uridine 5'-)P$^2$,P$^3$-methylenetriphosphate; P$^1$,P$^3$-di(uridine 5'-)P$^2$,P$^3$-difluoromethylenetriphosphate; P$^1$,P$^3$-di(uridine 5'-)P$^2$,P$^3$-imidotriphosphate; -di(4-thiouridine-5'-)triphosphate; P$^1$,P$^3$-di(3,N$^4$-ethenocytidine 5'-)triphosphate; P$^1$,P$^3$-di(imidazo[1,2-c]pyrimidine-5(6H)-one-2-(3-nitro)-phenyl-6-β-D-ribofuranoside 5'-)triphosphate; P$^1$-(inosine 5'-)P$^3$-(uridine 5'-)triphosphate; P$^1$-(4-thiouridine 5'-)P$^3$-(uridine 5'-)triphosphate; P$^1$-(cytosine β-D-arabinofuranoside 5'-)P$^3$-(uridine 5'-)triphosphate; P$^1$-(uridine 5'-)P$^3$-(xanthosine 5'-) triphosphate; P$^1$-(2'-deoxyuridine 5'-)P$^3$-(uridine 5'-)triphosphate; P$^1$-(3'-azido-3'-deoxythymidine 5'-)P$^3$-(uridine 5'-)triphosphate; P$^1$,P$^3$-di(3'-azido-3'-deoxythymidine 5'-) triphosphate; 2'(3')-benzoyl-P$^1$,P$^3$-di(uridine 5'-)triphosphate; P$^1$,P$^3$-di(2'(3')-benzoyl uridine 5'-)triphosphate; P$^1$-(2'-deoxyguanosine 5'-)P$^3$-(uridine 5'-)triphosphate; P$^1$-(2'-deoxyadenosine 5'-)P$^3$-(uridine 5'-)triphosphate; P$^1$-(2'-deoxyinosine 5'-)P$^3$-(uridine 5'-) triphosphate; P$^1$-(2'-deoxycytidine 5'-)P$^3$-(uridine 5'-)triphosphate; P$^1$-(4-thiouridine 5'-)P$^3$-(2'-deoxyuridine 5'-)triphosphate; P$^1$-(8-azaadenosine-5'-)P$^3$-(uridine 5'-)triphosphate; P$^1$-(6-mercaptopurine riboside 5'-)P$^3$-(uridine 5'-)triphosphate; P$^1$-(6-mercaptopurineriboside 5'-)P$^3$-(2'-deoxyuridine 5'-)triphosphate; P$^1$-(4-thiouridine 5'-)P$^3$-(arabinocytidine 5'-)triphosphate; P$^1$-(adenosine 5'-)P$^3$-(4-thiomethyluridine 5'-) triphosphate; P$^1$-(2'-deoxyadenosine 5'-)P$^3$-(6-thiohexylpurine riboside 5'-) triphosphate, and P$^1$-(6-octyloxypurineriboside 5'-)P$^3$-(uridine 5'-)triphosphate. These salts include hydrated salt forms and unhydrated salt forms. Preferably, the purity of an anionic dinucleoside triphosphate component with associated cations is >80% by weight, more preferably >90% by weight, and even more preferably >95% by weight in any hydrated- or non-hydrated solid form.

Dinucleoside polyphosphate salts of general Formula I further include dinucleoside diphosphate-disodium salts, -diammonium salts, -di(quaternary ammonium) salts, -dipotassium salts, -dilithium salts, -monosodium/monopotassium salts, -monopotassium/monolithium and -monosodium/monolithium salts. These salts include hydrated salt forms and unhydrated salt forms. Preferably, the purity of the anionic dinucleoside diphosphate component with associated cations is >80% by weight, more preferably >90% by weight, and even more preferably >95% by weight in any hydrated- or non-hydrated solid form.

An example of an anionic dinucleoside diphosphate component of such a salt is: P$^1$-(uridine 5'-)P$^2$-(4-thiouridine 5'-) diphosphate, where the salt can be in a hydrated or unhydrated form. Examples of associated cations are: potassium or sodium or both potassium and sodium.

Dinucleoside polyphosphate salts of general Formula I additionally include P$^1$,P$^5$-di(uridine 5'-)pentaphosphate salts; and P$^1$,P$^6$-di(uridine 5'-)hexaphosphate salts with five and six cation components respectively, independently selected from: sodium, potassium, lithium, ammonium and quaternary ammonium. Examples are the P$^1$-(2'-deoxycytidine 5'-)P$^5$-(uridine 5'-) pentaphosphate (dCP$_5$U) salts and P$^1$-(2'-deoxycytidine 5'-)P$^6$-(uridine 5'-) hexaphosphate (dCP$_6$U) salts with five and six cation components respectively, independently selected from: sodium, potassium, lithium, ammonium and quaternary ammonium, These salts can be in hydrated or unhydrated forms.

Another hydrolysis-resistant P2Y agonist is a nucleotide with a modified phosphate ester/anhydride backbone, e.g. a methylene, imido or other group that protects the phosphate ester, or anhydride bonds from being readily hydrolyzed. Dinucleotides are in general resistant to hydrolysis due to lack of a terminal phosphate group. Certain dinucleotides are especially resistant to hydrolysis. For example, a P$^1$-(2'-deoxycytidine 5')—P$^4$-(uridine 5'-)tetraphosphate salt is more resistant in comparison with a P$^1$,P$^4$-di(uridine 5'-)tetraphosphate salt.

Furthermore, groups placed on or in the phosphate chain of a mononucleotide impart some stability against hydrolysis, e.g. salts of simple alkyl phosphate esters (methyl, ethyl, benzyl, etc.) or salts of thiophosphate nucleotides (e.g. UTPγS) tend to have more stability against hydrolysis. Useful hydrolysis-resistant mononucleoside triphosphate salts for the present method include alkali metal salts of the following nucleotide derivatives (CA Index numbers and names of parent acids provided): 5'-UTPγS, [79049-97-1], CA Index Name: Uridine 5'-trihydrogen diphosphate, P'-anhydride with phosphorothioic acid; 5'-CTPγS, [439919-14-9], CA Index Name Cytidine 5'-trihydrogen diphosphate, P'-anhydride with phosphorothioic acid; 5'-TTPγS, [439919-15-0], CA Index Name: Thymidine 5'-trihydrogen diphosphate, P'-anhydride with phosphorothioic acid; 5'-GTPγS, [37589-80-3], CA Index Name: Guanosine 5'-trihydrogen diphosphate, P'-anhydride with phosphorothioic acid; 5'-CP$_2$NHP, [439919-16-1], CA Index Name: 5'-Cytidylic acid, monoanhydride with imidodiphosphoric acid; 5'-TP$_2$NHP, [439919-17-2], CA Index Name: 5'-Thymidylic acid, monoanhydride with imidodiphosphoric acid; 5'-UP$_2$NHP, [82145-58-2], CA Index Name: 5'-Uridylic acid, monoanhydride with imidodiphosphoric acid; 5'-GP$_2$NHP, [34273-04-6], CA Index Name: 5'-Guanylic acid, monoanhydride with imidodiphosphoric acid; 5'-AP$_2$NHP, [25612-73-1], CA Index Name: 5'-Adenylic acid, monoanhydride with imidodiphosphoric acid; 5'-ATPγS, [35094-46-3], CA Index Name: Adenosine 5'-trihydrogen diphosphate, P'-anhydride with phosphorothioic acid; α,β-methylene 5'-ATP, [7292-42-4], CA Index Name: Adenosine, 5'-[hydrogen [[hydroxyphosphonooxy-phosphinyl]methyl]phosphonate]; β,γ-methylene 5'-ATP, [3469-78-1], CA Index Name: 5'-Adenylic acid, monoanhydride with methylenebis[phosphonic acid]; 5'-ATPαS, [29220-54-0], CA Index Name: Adenosine, 5'→P"'-ester with thiotriphosphoric acid; β,γ-difluoromethylene 5'-UTP, 5'-Uridylic acid, monoanhydride with difluoromethylenebis[phosphonic acid]; β,γ-methylene 5'-UTP, [71850-06-1], CA Index Name: 5'-Uridylic acid, monoanhydride with methylenebis[phosphonic acid]; and β,γdichloromethylene 5'-UTP; 5'-Uridylic acid, monoanhydride with dichloromethylenebis[phosphonic acid].

The present invention also provides salts of Formula I, wherein the furanosyl sugar moieties of Formula I are selected from the group consisting of ribosyl, 2'-deoxyribofuranosyl, 3'-deoxyribofuranosyl, 2',3'-dideoxyribofuranosyl, arabinofuranosyl, 3'-deoxy-arabinofuranosyl, xylofuranosyl, 2'-deoxyxylofuranosyl, and lyxofuranosyl; and the salt forms comprise salts of sodium, potassium, lithium, ammonium, and/or quaternary ammonium ions.

The present invention further provides tetra-(alkali metal) salts (sodium, potassium, and lithium salts) of the following dinucleotide polyphosphates: P$^1$-(6-mercaptopurine-riboside 5'-) P$^4$-(uridine 5'-)tetraphosphate, P$^1$-(6-mercaptopurineriboside 5'-)P$^4$-(2'-deoxyuridine 5'-)tetraphosphate, P$^1$-(4-thiouridine 5'-)P$^4$-(arabinocytidine 5'-)tetraphosphate, P$^1$-(2'-deoxyadenosine 5'-)P$^4$-(6-thiohexylpurineriboside 5'-)tetraphosphate, P$^1$-(6-octyloxypurineriboside 5'-)P$^4$-(uridine 5'-)tetraphosphate, P$^1$-(arabinoadenosine-5')P$^4$-(uridine 5'-)tetraphosphate, P$^1$-(lyxofuranosylthymine 5'-)P$^4$-(uridine 5'-)tetraphosphate, and P$^1$-(xylofuranosyluracil 5'-)P$^4$-(uridine-5'-)tetraphosphate. These salts may be in hydrated or unhydrated form.

Compounds encompassed by the present invention can be prepared by condensation of a nucleoside mono-, di-, or triphosphate (which can be in the form of a tertiary amine salt), activated with a condensing agent such as, but not limited to, carbonyldiimidazole or dicyclohexylcarbodiimide, with a second molecule of the same or a different mono-, di-, or triphosphate (which also can be in the form of a tertiary amine salt) to form a desired dinucleotide polyphosphate material, such as in the form of a tertiary amine salt. Another method of preparation of tertiary ammonium salts of dinucleotide polyphosphates is the sequential condensation of a nucleoside phosphate tertiary ammonium salt, activated as above, with a non-nucleoside mono-, di- or polyphosphate tertiary ammonium salt, such as, but not limited to, a monophosphate or pyrophosphate anionic salt to yield the desired tertiary ammonium salt of the dinucleoside polyphosphate, the non-isolated intermediate in such a case being a mononucleoside polyphosphate tertiary ammonium salt. Yet another preparative approach is the sequential condensation of a mono-, di- or polyphosphate moiety, activated as mentioned above, or in the form of an acid halide or other derivative reactive toward nucleophilic displacement, with a nucleoside phosphate tertiary ammonium salt or polyphosphate tertiary ammonium salt to yield the desired dinucleoside polyphosphate tertiary ammonium salt. The desired dinucleoside polyphosphate tertiary ammonium salt can also be formed by modification of a pre-formed dinucleoside polyphosphate tertiary ammonium salt by substitution or derivatization of a moiety or moieties on the purine, pyrimidine or carbohydrate ring.

The tertiary ammonium salts of dinucleoside polyphosphates can be purified using chromatography methods known in the art, and can be converted into other salt forms using chromatographic methods or other chemical methods. Alkali metal salts, for example, can be synthesized from previously-purified ammonium salts of the appropriate dinucleoside polyphosphates wherein the corresponding amine is volatile (e.g., NHEt$_3^+$, or Bu$_3$NH$^+$ salts) by adding an appropriate amount of one or more alkali metal bases (e.g., one or more alkali metal hydroxide, carbonate, bicarbonate or acetate salts) to an aqueous solution of a polyammonium salt of a dinucleoside polyphosphate, and evaporating the resulting solution to dryness at reduced pressure and temperature (e.g., 40° C.). If needed, water can be added to the resulting material, and the evaporation process can be repeated to remove small amounts of remaining volatile amines and other volatile components from the remaining poly-(alkali metal)/polyphosphate salt combination.

Nucleoside phosphate materials used as starting materials are commercially available, or can be made from the corresponding nucleosides by methods well known to those skilled in the art. Likewise, where nucleosides are not commercially available, they can be made by modification of other readily available nucleosides, or by synthesis from heterocyclic and carbohydrate precursors by methods well known to those skilled in the art (WO 96/40059, WO 96/02554A1, WO-A-9815563, and WO 98/55494; Theoclitou, et al., *J. Chem. Sot. Perkin Trans.* I, 2009-2019 (1996); Guranowski, et al., *Nucleosides and Nucleotides* 14, 731-734 (1995); Visscher, et al., *Nucleic Acids Research* 20, 5749-5752 (1992); Holler, et al., *Biochemistry* 22, 4924-10 4933 (1983); Orr, et al., *Biochem. Pharmacol.* 673-677 (1988); Plateau, et al., *Biochemistry* 24, 914-922 (1985); Hagmeier, et al., *J. Chromatography* 237, 174-177 (1982); Scheffzek, et al., *Biochemistry* 35, 9716-9727 (1996); Stridh, et al., *Antiviral Res.,* 97-105 (19861); Tarasova, et al., *Chem. Abs.* 110, 154770 (1988); Hata, et al., *Chem. Lett.,* 987-990 (1976); Huhn, et al., 28, 1959-1970 (1993); Tumanov, et al., *Chem. Abs.* 109-6867d (1987); Pintor, et al., *Molecular Pharmacology* 51, 277-284 (1997); and U.S. Pat. Nos. 4,855,304; 5,635,160; 5,495,550; and 5,681,823).

Those having skill in the art will recognize that the starting materials can be varied and additional steps employed to produce compounds encompassed by the present invention. In some cases, protection of certain reactive functionalities is useful to achieve some of the above transformations. In general, the need for such protecting groups as well as the conditions necessary to attach and remove such groups will be apparent to those skilled in the art of organic synthesis.

The dinucleotide and nucleotide compounds of the present invention encompass non-toxic pharmaceutically acceptable salts including mixed-cation salts, and mixtures of the same. Examples include, but are not limited to, an alkali metal salt (such as a lithium, sodium or potassium salt) of a dinucleoside tetraphosphate of Formula I; an alkaline earth metal salt (such as a magnesium or calcium salt) of a dinucleoside triphosphate of Formula I; or an ammonium or quaternary ammonium salt, e.g., cations=$NX_4^+$ (wherein each X is independently H or $C_{1-4}$), of a dinucleoside tetraphosphate of Formula I, or a dinucleoside diphosphate of Formula I. Mixed-cation salts of dinucleoside polyphosphates (such as a disodium/dipotassium dinucleoside tetraphosphate salt or monopotassium/trisodium dinucleoside tetraphosphate salt are also contemplated for this invention. An example of such a mixed-alkali metal salt of a dinucleoside tetraphosphate is the monopotassium/trisodium salt of $P^1$-(2'-deoxycytidine 5')—$P^4$-(uridine 5'-)tetraphosphate.

Pharmaceutically acceptable salts are salts that retain the desired biological activity of the parent compound and do not impart undesired toxicological effects. The present invention also encompasses prodrugs of the compounds disclosed herein. Those skilled in the art will recognize various synthetic methodologies that can be employed to prepare the non-toxic pharmaceutically acceptable salts, and prodrug salts of the present invention.

Though the compounds of the present invention are primarily concerned with the treatment of human subjects, they can also be employed for the treatment of other mammalian subjects such as dogs, cats and horses for veterinary purposes.

The pharmaceutical utility of compounds of this invention is indicated by the inositol phosphate assay for $P2Y_2$ and other P2Y receptor activity. This widely used assay, as described in Lazarowski, et al. (*Brit. J. Pharm.* 116, 1619-27 (1995)), relies on the measurement of inositol phosphate formation as a measurement of activity of compounds activating receptors linked via G-proteins to phospholipase C. Another useful technique for evaluation of the pharmaceutical utility of the salts of Formula I employs a fluorescence-based, calcium-mobilization assay (using a fluorescence light imaging plate reader or FLIPR; Molecular Devices Corp., Sunnyvale, Calif.) and cloned human P2Y receptors stably expressed in 1321N1 human astrocytoma cells, for example, as described in Yerxa, et al. (*J. Pharm and Experimental Therapeutics* 302, 871-80, (2002)).

The efficacy of the compounds of Formula I and nucleotide salt derivatives with enhanced stability is reflected in their ability to facilitate removal of pathological fluid accumulation in sub-retinal and intra-retinal spaces associated with edematous retinal disorders including retinal detachment and retinal edema. The effective dose will depend on characteristics of the individual patient, activity of the specific compound employed, mode of administration, and characteristics of the disease or disorder, and can be determined by those skilled in the art.

Dosage levels to remove extraneous fluid within intra-retinal or subretinal spaces are of the range of 10 μg/eye to 10 mg/eye, preferably in the range 50 μg/eye to 6 mg/eye, and most preferably 0.1 mg/eye to 4 mg/eye.

Administration of Compounds

The active compounds disclosed herein can be administered to the eyes of a patient by any suitable means, but are preferably administered by administering a liquid or gel suspension of the active compound. Alternatively, the active compounds can be applied to the eye via liposomes. Further, the active compounds can be infused into the tear film via a pump-catheter system. Another embodiment of the present invention involves the active compound contained within a continuous or selective-release device, for example, membranes such as, but not limited to, those employed in the Ocuser™ System (Alza Corp., Palo Alto, Calif.). As an additional embodiment, the active compounds can be contained within, carried by, or attached to contact lenses that are placed on the eye. Another embodiment of the present invention involves the active compound contained within a swab or sponge that can be applied to the ocular surface. Another embodiment of the present invention involves the active compound contained within a liquid spray that can be applied to the ocular surface. Another embodiment of the present invention involves an injection of the active compound directly into the lachrymal tissues or onto the eye surface.

The active compounds disclosed herein can be administered by intravitreal, systemic, or topical administration. Intravitreal administration is a preferred route of administration. Intravitreal administration comprising: single or multiple intravitreal injections; administration directly into the vitreal chamber during surgery separately or in conjunction with intraocular irrigation solutions, or other similar solutions or devices routinely used during vitreoretinal surgery; administration via liposomes or other suitable pharmaceutical carriers; administration via continuous or selective-release intravitreal-implantable devices, including, but not limited to, Ocusert™ (Alza Corp., Palo, Alto, Calif.) and Vitrasert (Bausch and Lomb, Inc., Rochester, N.Y.). The vitreous concentration of the active compound ranges from 1-500 micromolar, and preferably, 2-200 micromolar.

In one embodiment of the invention, the active compound is injected in the form of an aqueous pharmaceutical composition into the vitreous in a total amount between about 0.10 milligrams and about 4.0 milligrams per eye. The aqueous pharmaceutical composition contains an active compound as a pharmaceutically acceptable salt, such as a sodium, potassium, lithium or tetraalkyl ammonium salt. The aqueous pharmaceutical composition in general has an osmolarity between about 250 and 350 mOsm, and pH between about 5.0 and 9.0; and preferably has an osmolarity between about 280 and 300 mOsm, and pH between about 7.0 and 7.6. The intravitreal injection can be performed by single or multiple intravitreal injections at injection volumes of 1-200 μl; preferably 5-100 μl. When the injection volume is small such as 1-25 μl, the pharmaceutical composition can have a broader osmolarity and pH range. When the injection volume is large such as 100-200 μl, the pharmaceutical composition preferably has a narrower osmolarity and pH range such as about 280-300 mOsm, and about 7.0-7.6 pH.

The intravitreal solution containing the active compound optionally contains a physiologically compatible vehicle, as those skilled in the ophthalmic art can select using conventional criteria. The vehicles are selected from the known ophthalmic vehicles which include, but are not limited to, saline solution, water soluble polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride. The preferred embodiment is an intravitreal solution comprising active compound and saline at about neutral pH and physiological osmolarity.

The topical solution containing the active compound can also contain a physiologically compatible vehicle, as those skilled in the ophthalmic art can select using conventional criteria. The vehicles are selected from the known ophthalmic vehicles which include, but are not limited to, saline solution, water soluble polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, there are various methods of administering the active compounds of the present invention systemically. One such means would involve an aerosol suspension of respirable particles comprised of the active compound, which the subject inhales. The active compound would be absorbed into the bloodstream via the lungs or contact the ocular tissues via the nasolacrimal ducts, and subsequently contact the retinal pigment epithelial cells in a pharmaceutically effective amount. The respirable particles can be liquid or solid, with a particle size sufficiently small to pass through the mouth and larynx upon inhalation; in general, particles ranging from about 1 to 10 microns, but more preferably 1-5 microns, in size are considered respirable.

Another means of systemically administering the active compounds to the eyes of the subject would involve administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing compounds of Formula I or hydrolysis-resistant nucleotide derivatives are in the form of tablets, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more agents selected from the group consisting of: sweetening agents, flavoring agents, coloring agents and preserving agents in order to provide pharmaceutically elegant and palatable preparations. Tablets contain the active ingredient in admixture with nontoxic pharmaceutically acceptable excipients that are suitable for the manufacture of tablets. These excipients include, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Additional means of systemic administration of the active compound to the eyes of the subject would involve a suppository form of the active compound, such that a therapeutically effective amount of the compound reaches the eyes via systemic absorption and circulation.

Further means of systemic administration of the active compound would involve direct intra-operative instillation of a gel, cream, solution or liquid suspension form of a therapeutically effective amount of the active compound.

The method of the present invention is useful to enhance the effects of surgery, pharmacotherapy, and adjunctive agents used to treat and manage disorders associated with retinal detachment and retinal edema. Surgical approaches include scleral buckle, pneumatic retinopexy, macular translocation and vitrectomy. Pharmacotherapeutic agents such as corticosteroids and acetazolamide have been used to manage macular edema.

High doses may be required for some therapeutic agents to achieve levels to effectuate the target response, but may often be associated with a greater frequency of dose-related adverse effects. Thus, combined use of the compounds of the present invention with agents commonly used to treat retinal detachment and retinal edema permits relatively lower doses of such agents resulting in a lower frequency of adverse side effects associated with long-term administration of such therapeutic agents. Thus, another indication of the compounds in this invention is to reduce adverse side effects of drugs used to treat retinal detachment and retinal edema, such as the development of systemic effects with acetazolamide.

The present invention provides alkali metal salts, including mixed-(alkali-cation) salts of dinucleoside polyphosphates. Preferred dinucleoside polyphosphates are tetraphosphate anhydrides esterified with a nucleoside (or nucleoside derivative) at each end of the tetraphosphate-anhydride chain, as shown in Formula I (where, for preferred compounds, n=m=1). Salts of dinucleoside tetraphosphates and derivatives comprise tetra-(alkali metal) salts, such as tetrasodium, tetralithium, tetrapotassium and tetra-(mixed alkali metal) salts. $P^1$-(2'-deoxycytidine 5'-) $P^4$-(uridine 5'-) tetraphosphate (i.e., $dCP_4U$), tetra-(alkali metal) salts, such as $dCP_4U$ tetrasodium salt, $dCP_4U$ tetralithium salt, $dCP_4U$ tetrapotassium salt and $dCP_4U$ tetra-(mixed alkali metal) salts are examples of this useful class of salts. Tetra-(mixed alkali metal) cation compositions of the tetra-(mixed alkali metal) salts of dCP4U include, for example, monosodium/tripotassium, disodium/dipotassium, trisodium/monopotassium, monopotassium/trilithium, dipotassium/dilithium, tripotassium/monolithium, monosodium/trilithium, disodium/dilithium, trisodium/monolithium, and monosodium/monolithium/dipotassium, monosodium/dilithium/monopotassium and disodium/monolithium/monopotassium cation compositions.

The present invention further provides polyammonium and poly(quaternary ammonium) salts of dinucleoside polyphosphates. Preferred dinucleoside polyphosphate salts are salts of tetraphosphate anhydrides esterified with a nucleoside (or nucleoside derivative) at each end of the tetraphosphate-anhydride chain, as shown in Formula I (where for these preferred compounds, n=m=1). Tetraammonium or tetra(quaternary ammonium) salts of dinucleoside tetraphosphates and dinucleoside tetraphosphate derivatives are examples of polyphosphate salts of the invention. Herein, the terms "ammonium salt or ammonium salts" are used to describe salts derived from ammonia as well as those derived from alkyl amines, dialkyl amines, trialkyl amines, aralkyl amines, aryl amines, quaternary ammonium salts, and related compounds. A "tetraammonium" salt, therefore, would include four ammonium units, e.g., four ($NH_4^+$) units, four (alkyl-$NH_3^+$) units, or four (dialkyl-$NH_2^+$) units, etc. from the types of ammonium groups included in the above definition. Quaternary ammonium salts include, but are not limited to: tetraalkylammonium salts, trialkylmonobenzylammonium salts, trialkylphenylammonium salts, dialkyldiarylammonium salts, tribenzylalkylammonium salts, etc. A "tetra(quaternary ammonium)" salt, therefore, would include four quaternary ammonium units, e.g., four ($Me_4N^+$) units, four (alkyl$_4$-$N^+$) units, or four (benzyl-$NMe_3^+$) units, etc. selected from the types of quaternary ammonium groups included in the above definition. Specific examples of useful ammonium salts of this invention are: $dCP_4U$ ($NH_4^+$)$_4$ salt, $dUP_4U$ ($NH_4^+$)$_4$ salt, $dCP_4U$ ($NBu_4^+$)$_4$ salt and $dCP_4U$ ($NHBu_3^+$)$_4$ salt. In the above, as common in the art, Me is the abbreviation of methyl, and Bu is the abbreviation of butyl.

The tetra-(alkali metal) salt compositions of dinucleoside tetraphosphates, and in a like manner, the tri-(alkali metal) salt compositions of dinucleoside triphosphates, the di-(alkali metal) salt compositions of dinucleoside diphosphates, or in general, the deprotonated polyphosphate-(alkali metal) salt composition of a dinucleoside polyphosphate where all acid phosphate groups are deprotonated are more resistant to hydrolysis than the corresponding mono-acid salts or di-acid salts, etc., and therefore provide an improved stability and a longer shelf life for storage.

Some of the advantages of tetra-(alkali metal) salts of dinucleoside tetraphosphates (and similarly, the tri-(alkali metal) salts of dinucleoside triphosphates, or the di-(alkali metal) salts of dinucleoside diphosphates) are that these salts are easily handled as fluffy, white solids, compared to an oil or gum as found with some amine salts. Furthermore, these alkali-metal salts are advantageous in that they can be readily purified by aqueous ion chromatography in which only volatile organic solvents and water are used as eluents. Preferably, the purity of an anionic dinucleoside polyphosphate component with associated metal cations of Formula I is high (>80%, preferably >90%, more preferably >95% purity by weight) in any hydrated- or unhydrated solid form, thus is suitable for pharmaceutical use. Or alternatively, these types of alkali metal salts can be synthesized from previously-purified ammonium salts of the appropriate dinucleoside polyphosphates wherein the corresponding amine is volatile (e.g., $NH_4^+$, $MeNH_3^+$, or $Me_2NH_2^+$ salts) by adding an appropriate amount of one or more alkali metal bases (e.g., one or more alkali metal hydroxide, carbonate, bicarbonate or acetate salts) to an aqueous solution of a polyammonium salt of a dinucleoside polyphosphate, and evaporating the resulting solution to dryness at reduced pressure and temperature (e.g., 40° C.). If needed, water can be added to the resulting material, and the evaporation process can be repeated to remove small amounts of remaining volatile amines and other volatile components from the remaining poly-(alkali metal)/polyphosphate salt combination.

The inorganic sodium, lithium, and potassium cations help impart excellent water solubility to the corresponding nucleotides and dinucleotides, and this is an advantage in cases where good aqueous solubility is important, such as in the formulation of aqueous solutions of dinucleotide drugs wherein high water solubility can be important for flexibility in the preparation of pharmaceutical formulations of varying concentrations.

The tetra-(alkali metal) salts of dinucleotide tetraphosphates, such as $P^1$-(2'-deoxycytidine 5'-) $P^4$-(uridine 5'-) tetraphosphate tetrasodium salt and -monopotassium/trisodium salt have additional advantages, for example, they provide good long-term stability profiles compared with those of divalent cation salts (e.g. $Ca^{2+}$, $Mg^{2+}$, $Mn^{2+}$), which can catalyze the hydrolysis of phosphate anhydride-esters. In addition, the tetra-(alkali metal) salts of many dinucleotides like $P^1$-(2'-deoxycytidine 5'-) $P^4$-(uridine 5'-) tetraphosphate tetrasodium salt are non-irritating to the lungs and eyes. In many cases, other cations may be irritating to the lungs, eyes, and other mucosal epithelia.

Some of the advantages of tetra-ammonium salts of dinucleoside tetraphosphates (and in a like manner, the tri-ammonium salts of dinucleoside triphosphates, or the di-ammonium salts of dinucleoside diphosphates) are that these salts can be readily purified by aqueous ion chromatography or reverse-phase chromatography in which only volatile organic solvents, volatile organic salts and water are used as eluents. The volatile components are removed from the collected fractions by evaporation at reduced pressure and temperature (ca. 40° C.) to yield the desired poly-ammonium dinucleoside polyphosphate salt in purified form. Preferably, the purity of an anionic polynucleoside polyphosphate component with associated ammonium cations of Formula I is high (>80%, preferably >90%, more preferably >95% purity by weight) in any hydrated- or unhydrated solid form, thus are suitable for pharmaceutical use. Alternatively, these ammonium salts can be useful intermediates for the synthesis of other pharmaceutical materials and compositions. $P^1$-(2'-deoxycytidine 5'-) $P^4$-(uridine 5'-) tetraphosphate-4($NH_4^+$) (i.e., $dCP_4U$ ($NH_4^+$)$_4$ salt) and $P^1$-(2'-deoxycytidine 5'-) $P^4$-(uridine 5'-) tetraphosphate-4($NHBu_3^+$) (i.e., $dCP_4U$ ($NHBu_3^+$)$_4$ salt) are examples of these types of versatile ammonium salts.

Though inorganic sodium, lithium, and potassium cations can help impart excellent water solubility to anionic dinucleoside polyphosphate partners, there are some instances where enhanced lipophilicity of a dinucleoside polyphosphate salt would be advantageous in a pharmaceutical formulation, such as in a controlled-release formulation for a drug. In such a case, a more-hydrophobic amine salt of a dinucleoside polyphosphate, e.g., the tri-(methyl anthranilate) salt of a dinucleoside triphosphate, or the tetra-(nicotinamide) salt of a dinucleoside tetraphosphate, or the tetra-(choline) salt of a dinucleoside tetraphosphate like $dCP_4U$ or $U_2P_4$, would be useful for enhancing the lipophilicity of the corresponding salt relative to the alkali-metal salt, while decreasing the water solubility of the polyphosphate pharmaceutical. In some cases, an added benefit of lipophilic organic-cation salts is that the solubility in warm organic solvents or warm solvent/water mixtures is increased and can allow for efficient purification of a drug substance by crystallization.

The present invention also provides a pharmaceutical formulation comprising a dinucleoside polyphosphate salt such as a tetra-(alkali metal) salt of $P^1$-(2'-deoxycytidine 5'-)$P^4$-(uridine 5'-)tetraphosphate, {e.g., $dCP_4U$ ($K_4$) salt, $dCP_4U$ ($Na_4$) salt or $dCP_4U$ ($Li_4$) salt} or a tetra-(mixed alkali metal) salt of $P^1$-(2'-deoxycytidine 5'-)$P^4$-(uridine 5'-)tetraphosphate, {e.g., $dCP_4U$ ($KNa_3$) salt} in a pharmaceutically acceptable carrier, in the form of an aqueous, a gel, a gel-like, a two-phase suspension, or a solid formulation. Pharmaceutically acceptable salts are salts that retain the desired biological activity of the active compound and do not impart undesired toxicological effects. Pharmaceutically acceptable salts of dinucleoside polyphosphates include alkali metal salts such as lithium, sodium and/or potassium salts; alkaline earth metal salts such as magnesium or calcium salts; or ammonium or quaternary-ammonium salts, i.e., $NX_4^+$ (e.g., wherein each X is independently H or $C_{1-4}$). The pharmaceutically acceptable carrier is a physiologically compatible vehicle, which includes, but is not limited to, aqueous electrolyte solutions, polyethers, polyvinyls, polymers of acrylic acid, lanolin, and glucosaminoglycans.

The present invention provides a pharmaceutical formulation comprising one or more $P^1$-(2'-deoxycytidine 5'-)$P^4$-(uridine 5'-) tetraphosphate, tetra-(alkali metal) salts, -tetra ammonium salts, or -tetra(quaternary ammonium) salts, in a pharmaceutically acceptable carrier.

In one embodiment, the present invention provides a pharmaceutical formulation comprising $P^1$-(2'-deoxycytidine 5'-)$P^4$-(uridine 5'-) tetraphosphate, tetra-(alkali metal) salt, in a pharmaceutically acceptable carrier, wherein the tetra-(alkali metal cations) of said salt are selected from the group consisting of: tetrasodium, tetralithium, tetrapotassium, monosodium/tripotassium, disodium/dipotassium, trisodium/monopotassium, monopotassium/trilithium, dipotassium/dilithium, tripotassium/monolithium, monosodium/trilithium, disodium/dilithium, trisodium/monolithium, monosodium/monolithium/dipotassium, monosodium/dilithium/monopotassium and disodium/monolithium/monopotassium; and mixtures thereof. The four alkali metal cations associated with $dCP_4U$ can be a mix of $Na^+$, $Li^+$, and $K^+$ in any ratio.

In another embodiment, the present invention provides a pharmaceutical formulation comprising a $P^1$-(2'-deoxycytidine 5'-)$P^4$-(uridine 5'-) tetraphosphate, tetra-ammonium salt or one or more -tetra(quaternary ammonium) salts, in a pharmaceutically acceptable carrier. The quaternary ammonium salt in the formulation, for example, is a tetraalkylammonium salt, trialkylphenylammonium salt, dialkyldiarylammonium salt, trialkylbenzylammonium salt or tribenzylalkylammonium salt. Alternatively, the ammonium- or quaternary ammonium cation components of a dinucleoside polyphosphate salt, e.g., a $P^1$-(2'-deoxycytidine 5'-)$P^4$-(uridine 5'-) tetraphosphate tetra(quaternary ammonium) salt, or a $P^1$-(2'-deoxycytidine 5'-)$P^4$-(uridine 5'-) tetraphosphate tetraammonium salt, or a $P^1$-(uridine 5'-)$P^4$-(uridine 5'-) tetraphosphate tetra(quaternary ammonium) salt, or a $P^1$-(uridine 5'-)$P^4$-(uridine 5'-) tetraphosphate tetraammonium salt useful in this invention can optionally be linked to, included in, or be a part of a polymer where the polymer is of a useful molecular weight, porosity and molecular composition for the desired use. Examples of such polymer-bound ammonium salts useful in this invention as cationic partners for dinucleoside polyphosphates in a pharmaceutical formulation are strong anion-exchange compositions including, or similar to, Bio-Rad AG1, AGMP-1M and Macro-Prep 25Q resins, and weak anion-exchange compositions including, or similar to, DEAE-cellulose, BioRad AG4-X4 and Bio-Rex5 resins, and DEAE anion-exchange resins. Examples of supporting polymers for covalently-linked, incorporated or attached cations useful in this invention are polystyrene, polyacrylamide, cellulose, styrene copolymers including styrene/divinylbenzene copolymers, and polyethyleneglycol copolymers. An example of a dinucleoside polyphosphate/polymer-linked cation composition useful in this invention comprises the $P^1$-(2'-deoxycytidine 5'-)$P^4$-(uridine 5'-) tetraphosphate form of a strong anion-exchange resin like BioRad AG1 resin in a pharmaceutical formulation. Another example of a dinucleoside polyphosphate/polymer-linked cation composition useful in this invention comprises the $P^1$-(uridine 5'-)$P^4$-(uridine 5'-) tetraphosphate form of a strong anion-exchange resin like BioRad AG1 resin in a pharmaceutical formulation.

When the pharmaceutical formulation of dinucleoside polyphosphate salt is in the form of an aqueous solution, it generally comprises physiologically safe excipients formulated to osmolarity between 250-350 mOsm and pH 5-9; preferably 280-300 mOsM and pH 7.0-7.6. When the pharmaceutical formulation is in the form of a gel or gel-like formulation, it is preferably a hyaluronic acid or hyaluronic acid-containing formulation approved for intraocular surgical use. When the pharmaceutical formulation is in the form of a solid formulation, it is preferably a lyophilized powder, liposome or a biodegradable polymer. In one embodiment of the invention, the pharmaceutical formulation is sterile.

The pharmaceutical formulation optionally comprises an intraocular irrigation solution approved for surgical use.

The pharmaceutical formulation of the present invention is useful in treating different diseases, including, but not limited to retinal detachment, dry eye, cystic fibrosis, chronic obstructive pulmonary disease, sinusitis, otitis media, and nasolacrimal duct obstruction. The pharmaceutical formulation in general comprises the active ingredient such as $P^1$-(2'-deoxycytidine 5'-)$P^4$-(uridine 5'-) tetraphosphate, tetra-monovalent alkali metal salt, tetraammonium salt, or tetra (quaternary ammonium) salt, in the amount of 0.1-10%, preferably 0.2-8%, or more preferably 0.5-5% by weight.

The invention is illustrated further by the following examples, which are not to be construed as limiting the invention in scope or spirit to the specific procedures described in them.

EXAMPLES

Example 1

Localization of $P2Y_2$-Receptor mRNA in Retina and RPE

Cellular localization of $P2Y_2$-receptor mRNA in fresh frozen cross-sections of albino rabbit retina/RPE/choroid tissue was investigated by using nonisotopic in situ hybridization techniques. FIG. 1 shows a representative in situ hybridization result from antisense and sense digoxigenin (DIG)-labeled riboprobes engineered based on the $P2Y_2$ receptor mRNA sequence. Hybridization of antisense and sense riboprobes was visualized by immunohistochemistry using alkaline phosphatase-conjugated anti DIG antibody, and DIG-specific signal was detected using a chromophore reaction against the alkaline phosphatase, yielding purple/black staining. The tissues were also counterstained with nuclear fast red. The control sense probe (right) shows no specific labeling. Labeling with the anti-sense probe showed $P2Y_2$ receptor mRNA localization in scattered nuclei in the ganglion cell and inner nuclear layers and through the inner segment layer of photoreceptors. Strong labeling throughout the RPE was also detected, and in endothelial cells of the choroidal blood vessels.

Example 2

Effects of Synthetic $P2Y_2$ Agonist $UP_4dC$ Tetrasodium Salt on Cloned Human $P2Y_2$ Receptors The dinucleotide, {$P^1$-(uridine 5-)-$P^4$-(2'-deoxycytidine 5'-)tetraphosphate tetrasodium salt}($UP_4dC$, or referred to as INS37217, was tested for its activity (potency, efficacy, and selectivity) at cloned human P2Y receptor subtypes, which were stably expressed in 1321N1 astrocytoma cells. Activity was assessed using two in vitro indices of cell activation: 1)

mobilization of intracellular calcium stores, and 2) accumulation of [$^3$H]-inositol phosphates ([3H]-IP). UP$_4$dC tetrasodium salt was evaluated for activity in both assays against cells expressing the P2Y$_1$, P2Y$_2$, P2Y$_4$, or P2Y$_6$ receptors.

Figure 2:
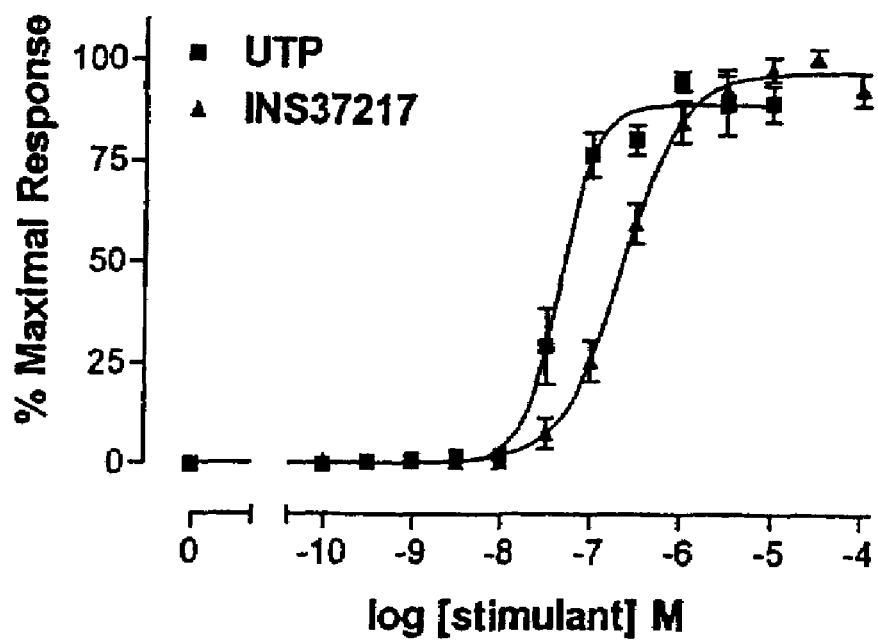
FIG. 2 represents the effects of the tetrasodium salt of $UP_4dC$ (INS37217) versus UTP on cytosolic calcium mobilization in 1321N1 cells overexpressing $P2Y_2$ receptor.

UTP tetrasodium salt and UP$_4$dC tetrasodium salt induced mobilization of cytosolic calcium in 1321N1 astrocytoma cells expressing human P2Y$_2$ (FIG. 2) receptors with EC$_{50}$ values of 0.22 µM and 0.8 µM, respectively. The calcium response to 100 µM UP$_4$dC tetrasodium salt was 100% of the maximal response to UTP tetrasodium salt at P2Y$_2$ receptors. In conclusion, UP$_4$dC tetrasodium salt is a full agonist for calcium mobilization at P2Y$_2$ receptors compared to UTP tetrasodium salt.

Figure 3:
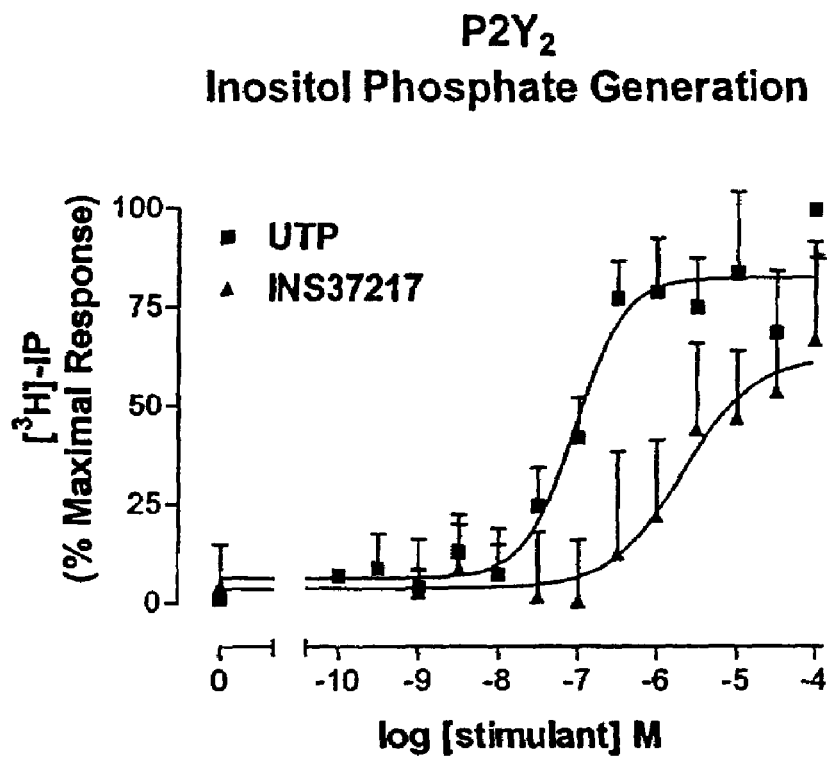
FIG. 3 represents the effect of the tetrasodium salt of $UP_4dC$ versus UTP on inositol phosphate generation in 1321N1 cells overexpressing $P2Y_2$ receptor.

UTP tetrasodium salt and UP$_4$dC tetrasodium salt stimulated [$^3$H]-IP accumulation in 1321N1 cells expressing human P2Y$_2$ (FIG. 3) receptors with EC$_{50}$ values of 1.1 and 2.2 µM, respectively. The inositol phosphate response to 100 µM UP$_4$dC tetrasodium salt was approximately that of the maximal response to UTP tetrasodium salt. In conclusion, UP$_4$dC tetrasodium salt is a full agonist for inositol phosphate release at P2Y$_2$ receptors compared to UTP tetrasodium salt in the test system.

Example 3

UP$_4$dC Tetrasodium Salt Stimulates Fluid Absorption in Freshly Isolated RPE Monolayers Fluid transport across freshly isolated, intact bovine and human fetal RPE monolayers was studied using a modified capacitance probe technique (Frambach, et al., *Biophys. J.* 47(4):547-52 (1985); Hughes, et al., *J Gen. Physiol.* 83(6): 875-99 (1984)).

The RPE was mounted vertically in a modified Ussing chamber such that apical and basolateral membranes were separately exposed to Ringer's solutions held in bathing reservoirs. Stainless steel capacitive probes were lowered into the apical and basolateral bathing reservoirs to sense the capacitance of the air gap between the probe and fluid meniscus. Fluid transport rate $J_v$ (µL cm$^{-2}$ hr$^{-1}$) was determined by monitoring fluid movement-induced changes in the air gap capacitance at the apical and basolateral baths.

Figure 4:
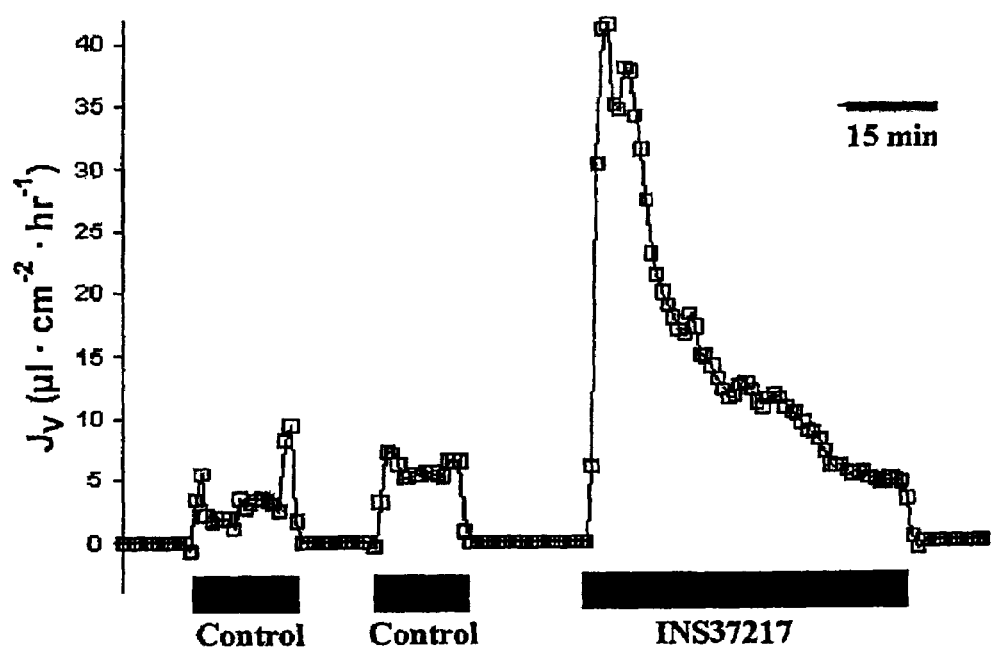
FIG. 4 represents the effects of the tetrasodium salt of $UP_4dC$ on fluid absorption in human fetal RPE.

Representative effects of agonist on J$_v$ in human fetal RPE are shown in FIG. 4. Positive J$_v$ values reflect fluid absorption (apical-to-basolateral) and negative J$_v$ values reflect fluid secretion (basolateral-to-apical). In the experiment shown in FIG. 4, control fluid movement across the freshly isolated human fetal RPE monolayer is absorptive at a rate of ~5 µL cm$^{-2}$ hr$^{-1}$. The addition of 50 µM agonist to Ringer's solution bathing the apical membrane elicited a transient increase in fluid absorption to ~40 µL cm$^{-2}$ hr$^{-1}$ before returning back to pre-stimulated levels. During the 1-hour treatment period, UP$_4$dC tetrasodium salt increased total fluid absorption by approximately a factor of three.

Figure 5:
FIG. 5 represents the effects of the tetrasodium salt of $UP_4dC$ on the magnitude and direction of fluid transport in bovine RPE.

Although the RPE is normally a fluid-absorbing epithelium, fluid secretion has occasionally been observed in freshly isolated RPE preparations. It has been postulated that fluid secretion in vivo may be a normal component of RPE physiology under certain conditions, such as following a transition between dark and light, or under pathological conditions, such as in serous retinal detachments. FIG. 5 shows that in a freshly isolated bovine RPE monolayer in which J$_v$ secretion is observed under control conditions, the agonist can reverse the direction of fluid transport to absorption. The effects of agonist are reversible upon returning to control Ringer's solution. Such an effect of agonist in vivo will offer therapeutic potential in the treatment of serous retinal detachments, such as central serous retinopathy, in which abnormal RPE-mediated fluid secretion is postulated to mediate the effects of transport of choroidal fluid into the subretinal space.

Example 4

Figure 6:
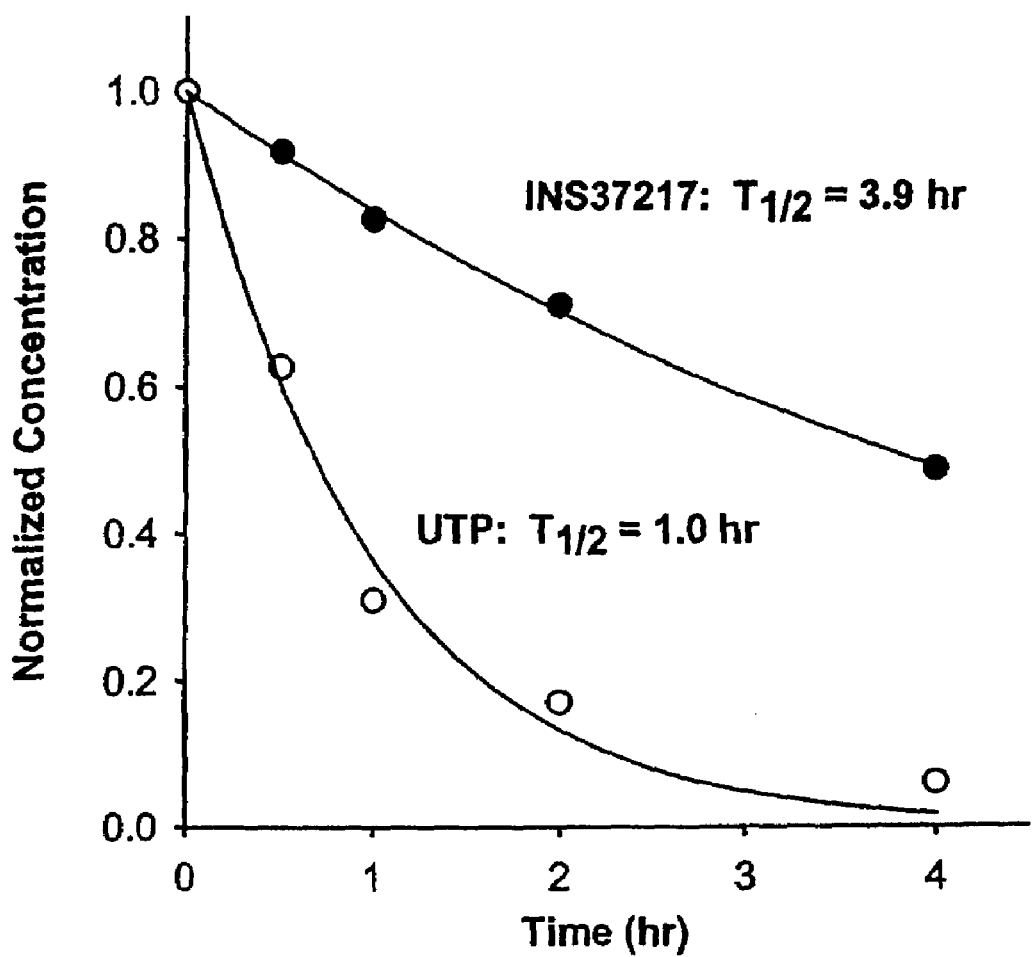
FIG. 6 represents the metabolism rates of the tetrasodium salt of $UP_4dC$ and UTP from freshly isolated pig retinal tissue.

Comparisons of Metabolic Stability of UP$_4$dC Tetrasodium Salt and UTP Tetrasodium Salt in Freshly Isolated Retinal Tissue The metabolism rate of UP$_4$dC tetrasodium salt and UTP tetrasodium salt in freshly isolated pig retinal tissue was determined using a high performance liquid chromatography (HPLC) method with UV-coupled detection. Freshly isolated retinal tissues of uniform size were isolated from euthanized young pigs (2-3 months) and retinal tissues were individually placed in an incubation chamber at 37° C. After an equilibration period of 30 minutes, each tissue was spiked with 100 µM UP$_4$dC tetrasodium salt or UTP tetrasodium salt in physiological buffer, and incubated for 0.5, 1, 2, and 4 hours. An aliquot of buffer from each chamber well was then processed for UV-coupled HPLC detection for chromatograms of the parent UP$_4$dC and UTP compounds at each time point to track the metabolism rates of each parent compound. FIG. 6 shows that UP$_4$dC tetrasodium salt has a four-fold greater metabolic half-life than UTP tetrasodium salt under these experimental conditions.

Example 5

Effects of Subretinal and Intravitreal UP$_4$dC Tetrasodium Salt in Rabbit Models Methods Surgical Procedure for Inducing Subretinal Blebs New Zealand White rabbits weighing approximately 1.5 kg (2-3 month old) were anesthetized with an intramuscular injection of 0.3 ml ketamine hydrochloride (100 mg/ml) and 0.5 ml xylazine hydrochloride (100 mg/ml) per kilogram body weight. Ketamine hydrochloride was added as needed. For experiments requiring observation of the fundus, the pupil was dilated with scopolamine hydrobromide 0.25%, cyclogyl 1% and phenylephrine hydrochloride 2.5% eyedrops.

One local retinal detachment was created in each eye. A wire lid speculum was placed and a segmental conjunctival peritomy (of approximately 2 clock hours) was made at the 3 and 9 o'clock positions. Two scleral incisions were made with a 19 gauge MVR-blade 0.5 mm posterior to the limbus through the ciliary body. A self-retaining planoconcave contact lens was placed on the corneal surface. A chandelier light, which was used for illumination, (Grieshaber & Co., AG Schaffhausen, Switzerland) was carefully guided through one of the sclerotomy sites into the vitreous cavity to avoid touching the lens.

Retinal detachments were made with a beveled 36 gauge retinal needle (Grieshaber & Co., AG Schaffhausen, Switzerland) attached by an extension tube to a 1 ml syringe that was driven by a calibrated, mechanical syringe pump (model 351, Sage Instruments, Cambridge, Mass.). Under direct observation with an operating microscope, the retinal needle was inserted through the second sclerotomy and slowly advanced to either the nasal or temporal myelin wing. These sites were selected for injection as the myelin wing gives additional structural support when compared to the adjacent areas of thin, avascular retina. The intraocular pressure was maintained at a low level to allow a slow hydrodissection of the fragile retina from the RPE. The tip of the 36 gauge needle was carefully inserted under the myelin wing. A localized dome-shaped detachment of the retina was created by using a mechanical syringe pump to inject ~50 μl of phosphate buffered saline fluid into the subretinal space. The instruments were removed from the eye and the sclerotomy sites remained open to keep the intraocular pressure constant. Although these experimental retinal detachments have a very small retinal hole, they behave functionally like non-rhegmatogenous retinal detachments and have been used to study mechanisms of subretinal fluid reabsorption.

Injection Solution

Modified phosphate buffered saline (MPBS) solution, used for all subretinal and intravitreal injections, was composed of 13.6 mM $Na_2HPO_4$, 6.2 mM $NaH_2PO_4$, 130.5 mM NaCl and 5 mM KCl, had an osmolarity of ~300 mOsm and a pH 7.2. $UP_4dC$ tetrasodium salt (MW 862) was added to the MPBS solution to achieve a target drug concentration of 12 mM, 1.4 mM, 1.0 mM or 0.15 mM. The experimental and control solutions were kept at equal osmolarity. For concentrations of 1 mM $UP_4dC$ tetrasodium salt or less, an appropriate amount of NaCl was added to the MPBS solution to compensate for the osmolarity contribution of $UP_4dC$ tetrasodium salt (1 mM $UP_4dC$ tetrasodium salt contributes ~4-5 mOsm). For concentrations greater than 1 mM $UP_4dC$ tetrasodium salt, solution isotonicity was maintained by reducing an equal osmolar of NaCl in the MPBS solution in place of the addition of $UP_4dC$ tetrasodium salt. All experimental and control solutions for each dosing cohort were formulated such that the final osmolarities were ±2 mOsm of each other. Sterile solutions were provided and evaluated under investigator-masked conditions.

Study Design

For each animal, one eye served as the experimental eye and the contralateral eye served as control. $UP_4dC$ tetrasodium salt was delivered either subretinally or intravitreally to evaluate its effects on reabsorption of subretinal fluid in experimentally induced retinal detachments. In the first series of experiments, MPBS solution with or without $UP_4dC$ tetrasodium salt (1 mM) was injected into the subretinal space. In the second series of experiments, a subretinal bleb containing MPBS solution was created, and then 50 μl of MPBS solution with or without $UP_4dC$ tetrasodium salt (12 mM, 1.4 mM, and 0.15 mM) was administered into the vitreous cavity with a 100 μl Hamilton syringe adjacent to the subretinal bleb. The surgeon was masked with respect to the content of the administered solutions.

Postoperative Observation

The corneal epithelium was protected with a layer of methylcellulose to maintain corneal clarity. Fundus photographs were obtained with a fundus camera (TRC-W, TOPCON, Japan) in selected cases. The observer determined by indirect opthalmoscopy the initial bleb size, and bleb size at 30-minute intervals for 3 hours. The vertical and horizontal dimensions of each subretinal bleb were recorded in disc diameters, using the adjacent optic disc as a reference marker. (The mean reference diameter of the optic disc is approximately 1 mm, as previously determined under a microscope in 10 enucleated eyes from albino rabbits). Bleb size at each evaluation time point was first quantified by multiplying the vertical and horizontal dimensions, and then expressing the resultant value as a dimensionless ratio relative to the initial size of each bleb. This dimensionless (normalized) bleb size at each evaluation time point was then plotted and analyzed as a function of time.

Results

Effects of Subretinal and Intravitreal $UP_4dC$ Tetrasodium Salt

Figure 7:
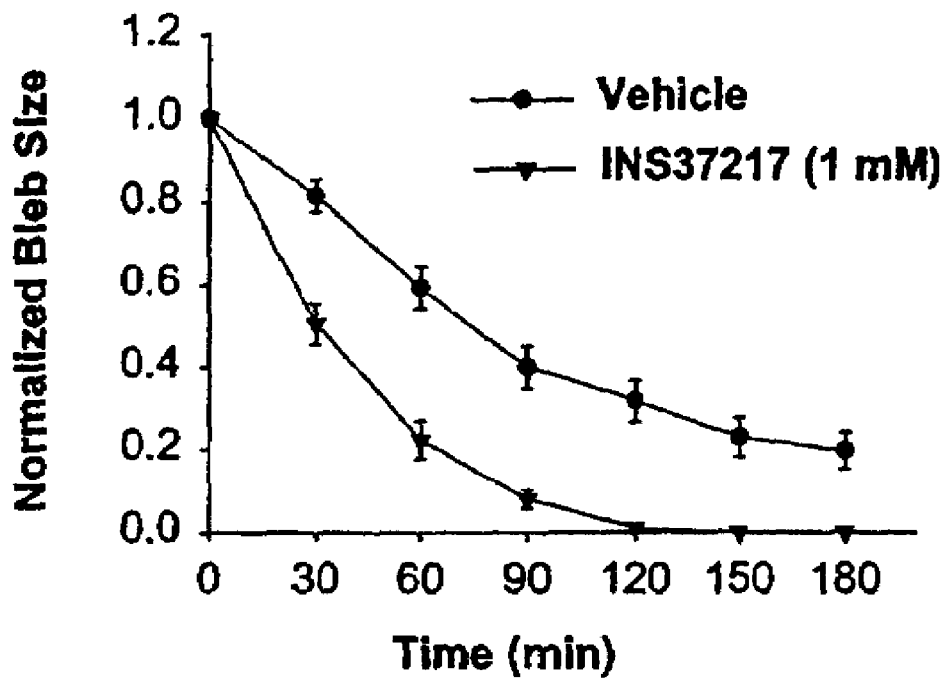
FIG. 7 shows the effects of subretinal the tetrasodium salt of $UP_4dC$ on the reabsorption of subretinal blebs. Subretinal blebs were created by injecting MPBS solution into the subretinal space with or without the tetrasodium salt of $UP_4dC$ (1 mM). Summarized results (mean±SEM) show that the tetrasodium salt of $UP_4dC$ increased the rate of clearance of subretinal blebs when compared with vehicle control.

In the first series of experiments, an isotonic MPBS solution containing 1 mM $UP_4dC$ tetrasodium salt was injected directly into the subretinal space. The contralateral eye received a subretinal injection of isotonic MPBS solution alone. FIG. 7 shows that $UP_4dC$-containing subretinal blebs resolved significantly faster than blebs containing MPBS solution alone. Reattachment of the retina was observed at 120-150 minutes in the $UP_4dC$-treated blebs, whereas the control subretinal blebs did not resolve over the 3 hour observation period. There was a significant difference in subretinal reabsorption at 30, 60, and 90 minutes using repeated measures ANOVA ($p<0.05$).

Figure 8:
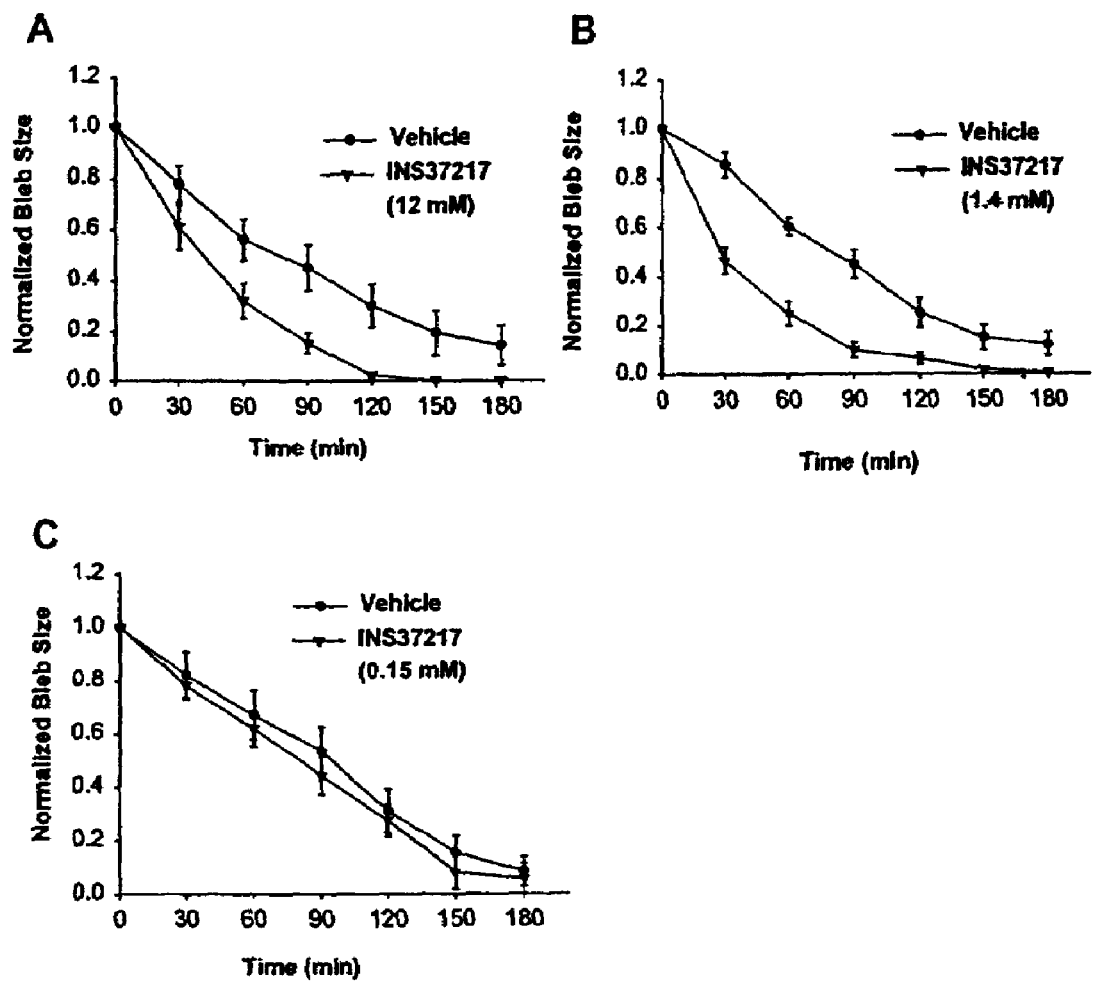
FIG. 8 (A-C) shows the effects of intravitreal injection of the tetrasodium salt of $UP_4dC$ on the reabsorption of subretinal blebs. MPBS solution was injected into the subretinal space to create subretinal blebs, followed immediately by an intravitreal injection of MPBS solution with or without the tetrasodium salt of $UP_4dC$ (12 mM, 1.4 mM, and 0.15 mM). Summarized results show that the tetrasodium salt of $UP_4dC$ administered at 12 and 1.4 mM, but not 0.15 mM, increased the rate of clearance of subretinal blebs when compared with vehicle control.

In the second series of experiments, subretinal blebs were first induced with MPBS solution and then followed immediately with a 50 μl intravitreal injection of MPBS solution with or without $UP_4dC$ tetrasodium salt (12, 1.4, and 0.15 mM) just adjacent to the bleb. FIGS. 8A & B shows that the two higher doses of $UP_4dC$ tetrasodium salt significantly enhanced the rate of subretinal bleb reabsorption and retinal reattachment when compared with vehicle. There was a statistically significant difference in the reabsorption rate between the eye treated with $UP_4dC$ tetrasodium salt and the vehicle alone at 30, 60, and 90 minutes ($p<0.05$). $UP_4dC$-treated eyes showed near complete retinal reattachment by ~90 min, whereas control blebs had not completely reabsorbed at 180 min.

FIG. 8C shows the reabsorption rate of subretinal bleb in eyes treated with 0.15 mM intravitreal $UP_4dC$ tetrasodium salt or vehicle alone. There was no statistically significant difference in the reabsorption of subretinal fluid at any time point in eyes with 0.15 mM $UP_4dC$ tetrasodium salt compared to vehicle alone.

Example 6

Effects of $UP_4dC$ Tetrasodium Salt on Retinal Reattachment in Rat Models Methods In vivo Preparation: Rat Study Design Retinal detachments were created in Long-Evans female rats by injecting 2-3 μl of modified phosphate buffer saline (MPBS) Ringer solution into the subretinal space; only one eye per rat was used. Using a CCD camera, images of the subretinal blebs were obtained at one-minute intervals for several hours. The acquisition of images is described in further detail below. In the control part of each experiment (at 0 to 30 min following creation of the retinal detachment), apparent bleb size reached a steady-state size, which remained unchanged during the course of anesthesia (several hours). MPBS solutions with or without $UP_4dC$ tetrasodium salt (5 mM) were formulated and injected (3 μl) into the vitreous of the rat eye under masked and randomized conditions. The vials and their contents were indistinguishable. After vitreous injection, the apparent bleb size either increased or decreased monotonically or was constant over the next 60 min as judged by the experimenter using the seven rank scale (0±3) illustrated in FIG. 9. Ranks were assigned by observing the change in apparent bleb size between 30-90 minutes after drug or placebo vitreous injection. Animals were re-anesthetized the next day and a separate estimate of rank was obtained. A rank of negative 3 means that the retinal bleb was apparently flattened. A rank of positive three means that the bleb approximately doubled in size. A zero rank means that the apparent bleb size was unchanged over time. After all of the experiments were completed, the content of each vial was unmasked and compared with the experimenter's conclusions based on the observation of images obtained between 30 and 90 minutes and at one day following administration of drug or placebo.

Results

Figure 9:
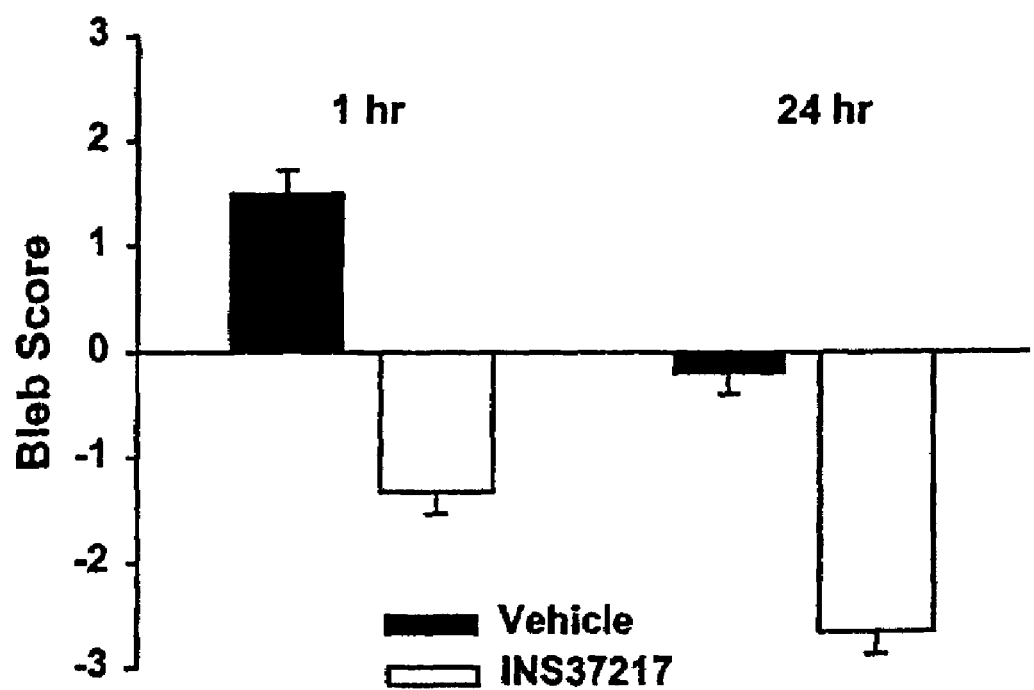
FIG. 9 shows a significant difference ($p<0.05$) between the tetrasodium salt of $UP_4dC$ (open bars) and vehicle control (placebo, solid bars) on the scoring of subretinal blebs.

The effects of intravitreal UP$_4$dC tetrasodium salt on retinal reattachment in 12 rats (1 eye/animal was dosed) are shown in FIG. 9. The experiments were carried out in a masked fashion to provide a rigorous and objective evaluation of the effects of UP$_4$dC tetrasodium salt on fluid reabsorption from experimentally produced subretinal blebs. In these experiments, after the creation of blebs, drug or placebo solutions were injected into the vitreous of the rat eye in a masked fashion (vials and their contents were indistinguishable). After all 12 eyes were scored, the key was unmasked and compared with the summarized results based on the observations at 1 and 24 hours. The results summarized in FIG. 9 show a significant difference ($p<0.05$) between UP$_4$dC tetrasodium salt (open bars) and vehicle control (placebo, solid bars) on the scoring of subretinal blebs. After one hour of treatment, the UP$_4$dC-treated eyes all showed a decrease in bleb size, whereas the control eyes all showed an increase in bleb size. The next day, the subretinal blebs from the UP$_4$dC-treated eyes had almost completely disappeared, whereas the subretinal blebs from the vehicle-treated eyes remained essentially unchanged. In 4 out of 6 UP$_4$dC-treated eyes, the retina appeared completely flat at the 24-hr time point.

Example 7

Primary Treatment for Subject with Macula-Off Rhegmatogenous Retinal Detachment

A patient presents with sudden onset of loss of central vision and is diagnosed with macula-off rhegmatogenous retinal detachment with a single break in the superior retina that is less than one clock hour in size. The patient's conjunctiva (cul de sacs) is sterilized with topical Betadine and by scrubbing and draping the face and lashes and lids. Local anesthesia is given via subconjunctival injection of xylocalne.

A patient is then given a single, slowly administered 50 µL-intravitreal injection of a sterile pharmaceutical composition by insertion of a 29 or 30 gauge needle from a 0.25 cc or 0.50 cc tuberculin syringe through the sclera in the pars plana region of the eye. The pharmaceutical composition consists of a metabolically resistant P2Y$_2$ receptor agonist formulated to isotonicity (280-300 mOsm) and physiological pH (7.0-7.5) in saline. The amount of active compound (P2Y agonist) administered to the eye is in the range of about 0.10 milligrams and about 4.0 milligrams.

The patient's eyes are bilaterally patched and the patient remains rested in a horizontal position for 4 hours, at which time the eyes are examined for retinal reattachment. If the retina has not completely reattached at the four-hour time point, the patient's eyes remain bilaterally patched until the next day (20-24 hours post dosing), at which point the retina is reexamined for reattachment. Following retinal reattachment, the retinal tear is suitably treated by conventional methods such as cryotherapy or laser photocoagulation.

Example 8

The Structure Elucidation of P$^1$-(2'-Deoxycytidine 5'-)P$^4$-(uridine 5'-) Tetraphosphate Tetrasodium Salt Due to the lack of adequate spectroscopic data of nonadenylated dinucleotides in the literature, a full structure elucidation of P$^1$-(2'-deoxycytidine 5'-)P$^4$-(uridine 5'-) tetraphosphate tetrasodium salt was performed by employing modern analytical techniques. The molecular mass was determined by mass spectrometry to be 861 [(M−H$^+$) m/z 862], confirming the molecular formula $C_{18}H_{23}N_5O_{21}P_4 \cdot 4Na$. Karl Fisher moisture analysis gave a value of 6.598% $H_2O$ and further confirmation of the molecular formula was obtained from elemental analysis: calculated for Na=9.97, found=9.99%, based on the molecular formula: $C_{18}H_{23}N_5O_{21}P_4 \cdot 4Na \cdot 3.4H_2O$ (FW=922.1 g/mol). The infrared spectrum showed a broad signal at 3417 cm$^{-1}$ and signals at 1677 and 1651 cm$^{-1}$, indicating the presence of hydroxyl (O—H stretch) and carbonyl (C=O stretch) functional groups. In addition, a phosphate (P=O stretch) was observed at 1249 cm$^{-1}$. The UV spectrum in water displayed a $\lambda_{max}$ of 265.8 nm.

The NMR spectra are: $^1$H NMR (D$_2$O, TMS) δ 2.16 (m, 1H), 2.30 (m, 1H), 4.08 (m, 1H), 4.09 (m, 1H), 4.13 (m, 1H), 4.14 (m, 2H), 4.16 (m, 1H), 4.27 (m, 2H), 4.49 (m, 1H), 5.85 (d, J=8.2 Hz, 1H), 5.86 (d, J=4.8 Hz, 1H), 6.01 (d, J=7.5 Hz, 1H), 6.19 (m, 1H), 7.79 (d, J=8.2 Hz, 1H), 7.81 (d, J=7.5 Hz, 1H); $^{13}$C NMR (D$_2$O, TMS) δ 39.3, 64.9 (d, J=4.5 Hz), 65.2 (d, J=4.7 Hz), 69.4, 70.5, 73.6, 83.2 (d, J=9.4 Hz), 85.3 (d, J=10 Hz), 85.7, 88.0, 96.4, 102.5, 141.4, 141.4, 151.6, 157.4, 165.9, 166.0; $^{31}$P NMR (D$_2$O, H$_3$PO$_4$) δ -21.5 (m), −10.3 (m).

Example 9

Method for the Large Scale Production of P$^1$-(2'-Deoxycytidine 5'-)P$^4$-(uridine 5'-) Tetraphosphate, Disodiumdipotassium Salt From P$^1$-(2'-Deoxycytidine 5'-)P$^4$-(uridine 5'-) Tetraphosphate, Tetraammonium Salt Approximately one kilogram of P$^1$-(2'-deoxycytidine 5'-)P$^4$-(uridine 5'-) tetraphosphate, tetraammonium salt {dCP$_4$U.(NH$_4$)$_4$} is dissolved in a sufficient amount of deionized water to form a ca. 5% solution. The amount of dCP$_4$U tetraammonium salt present in the solution is quantitated by comparison of the ultraviolet absorption at $\lambda_{max}$ 263 nm of an accurately diluted sample with that of a standard solution of P$^1$-(2'-deoxycytidine 5'-)P$^4$-(uridine 5'-) tetraphosphate, tetraammonium salt at 0.100 mg/mL. This solution of P$^1$-(2'-Deoxycytidine 5'-)P$^4$-(uridine 5'-) tetraphosphate, tetraammonium salt of known concentration is then cooled to 0° C. and treated with an ice cold solution containing two equivalents of sodium acetate and two equivalents of potassium bicarbonate in deionized water over two hours. The resulting solution is placed on a large rotary evaporator in portions and is concentrated under vacuum at below 60° C. to give a thick liquid, which is dissolved in deionized water to give a ca. 10% solution. The evaporation and dilution processes are repeated two more times to remove volatile ammonium salts, etc., and then the residue is dissolved in water to form a ca. 10% solution which is lyophilized to yield dCP$_4$U, disodiumdipotassium salt as a white solid in excellent yield and purity.

Example 10

Solubility and Stability of P$^1$-(2'-Deoxycytidine 5'-)P$^4$-(uridine 5'-) tetraphosphate, Monolithiummonopotassiumdisodium Salt The solubility of P$^1$-(2'-deoxycytidine 5'-)P$^4$-(uridine 5'-)-tetraphosphate, monolithiummonopotassiumdisodium salt in water is determined by adding portions of solid to a known volume of deionized water until the solution becomes turbid. Stability studies are performed by incubating the solid or aqueous solutions at low (5° C.) and elevated temperatures (40° C.) for a period of time. The monolithiummonopotassiumdisodium salt of P$^1$-(2'-deoxycytidine 5'-)P$^4$-(uridine 5'-) tetraphosphate is determined to have an excellent solubility and stability profile suitable for pharmaceutical applications.

Example 11

Solubility and Stability of P$^1$-(2'-Deoxycytidine 5'-)P$^4$-(uridine 5'-) tetraphosphate, Monopotassiumtrilithium Salt The solubility of P$^1$-(2'-deoxycytidine 5'-)P$^4$-(uridine 5'-) tetraphosphate, monopotassiumtrilithium salt in water is determined by adding portions of solid to a known volume of deionized water until the solution became turbid. Stability studies are performed by incubating the solid or aqueous solutions at low (5° C.) and elevated temperatures (40° C.) for a period of time. The monopotassiumtrilithium salt of P$^1$-(2'-deoxycytidine 5'-)P$^4$-(uridine 5'-) tetraphosphate is determined to have an excellent solubility and stability profile suitable for pharmaceutical applications.

Example 12

Toxicity of P$^1$-(2'-Deoxycytidine 5'-)P$^4$-(uridine 5'-) tetraphosphate, Monopotassiumtrisodium Salt in Animals The nonclinical toxicologic profile of P$^1$-(2'-deoxycytidine 5'-)P$^4$-(uridine 5'-) tetraphosphate, monopotassiumtrisodium salt is evaluated in a battery of genetic toxicology assays that include the bacterial reverse mutation assay, the in vitro mammalian cytogenetic test, the in vitro mammalian cell gene mutation test, and the micronucleus cytogenetic assay in mice. A study in rabbits examines local ocular tolerance and subchronic ocular toxicity after multiple daily administrations over a six-week period. No adverse findings are seen in the ocular toxicology studies. The P$^1$-(2'-deoxycytidine 5'-)P$^4$-(uridine 5'-) tetraphosphate, monopotassiumtrisodium salt has an excellent toxicology profile with a wide safety margin.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of treating cystic fibrosis in a subject in need thereof, said method comprising:
    administering to a subject suffering from cystic fibrosis P$^1$-(2'-deoxycytidine 5'-)P$^4$-(uridine 5'-)tetraphosphate, tetra-sodium salt, in an amount effective to treat cystic fibrosis.

2. A method of treating cystic fibrosis in a subject in need thereof, said method comprising:
    administering to a subject suffering from cystic fibrosis P$^1$-(2'-deoxycytidine 5'-)P$^4$-(uridine 5'-)tetraphosphate, tetra-(alkali metal) salt, in an amount effective to treat cystic fibrosis, wherein the tetra-(alkali metal) cations of said salt are tetralithium or tetrapotassium.

3. The method according to claim 2, wherein the tetra-(alkali metal) cations of said salt are tetralithium.

4. The method according to claim 2, wherein the tetra-(alkali metal) cations of said salt are tetrapotassium.

5. A method of treating cystic fibrosis in a subject in need thereof, said method comprising:
    administering to a subject suffering from cystic fibrosis P$^1$-(2'-deoxycytidine 5'-)P$^4$-(uridine 5'-)tetraphosphate, tetra-(alkali metal) salt, in an amount effective to treat cystic fibrosis, wherein the tetra-(alkali metal) cations of said salt are selected from the group consisting of:
    monosodium/tripotassium, disodium/dipotassium, trisodium/monopotassium,
    monopotassium/trilithium, dipotassium/dilithium, tripotassium/monolithium,
    monosodium/trilithium, disodium/dilithium, trisodium/monolithium,
    monosodium/monolithium/dipotassium, monosodium/dilithium/monopotassium and disodium/monolithium/monopotassium; and mixtures thereof.

* * * * *